US009561337B2

(12) United States Patent
Clement et al.

(10) Patent No.: US 9,561,337 B2
(45) Date of Patent: Feb. 7, 2017

(54) ACTIVE SYSTEM FOR IN-SITU CLEARING OF SECRETIONS AND OCCLUSIONS IN TUBES

(71) Applicant: Actuated Medical, Inc., Bellefonte, PA (US)

(72) Inventors: Ryan S Clement, State College, PA (US); Roger B Bagwell, Bellefonte, PA (US); Katherine M Erdley, Boalsburg, PA (US); Brian M Park, Bellefonte, PA (US); Casey A Scruggs, Middleburg, PA (US); Maureen L Mulvihill, Bellefonte, PA (US); Gabriela Hernandez Meza, Philadelphia, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 503 days.

(21) Appl. No.: 14/052,278

(22) Filed: Oct. 11, 2013

(65) Prior Publication Data
US 2014/0102445 A1 Apr. 17, 2014

Related U.S. Application Data

(60) Provisional application No. 61/712,437, filed on Oct. 11, 2012.

(51) Int. Cl.
*A61M 25/00* (2006.01)
*A61M 1/00* (2006.01)
*A61M 16/04* (2006.01)

(52) U.S. Cl.
CPC ....... *A61M 16/0463* (2013.01); *A61M 1/0058* (2013.01); *A61M 25/00* (2013.01);
(Continued)

(58) Field of Classification Search
CPC ............ A61M 16/0463; A61M 1/0058; A61M 2025/0019; A61M 2209/10; B08B 2209/027
See application file for complete search history.

(56) References Cited

U.S. PATENT DOCUMENTS 3,991,762 A 11/1976 Radford
4,638,539 A 1/1987 Palmer
(Continued)

FOREIGN PATENT DOCUMENTS

EP 1 666 168 A1 6/2006
JP 17 2005-296092 10/2005
(Continued)

OTHER PUBLICATIONS

International Searching Authority; International Search Report and Written Opinion of the International Searching Authority; International Application No. PCT/US2013/064642; Patent Cooperation Treaty; pp. 1-11; publisher United States International Searching Authority; Published Alexandria, Virginia, United States of America; copyright and mailing date Jan. 16, 2014; copy enclosed (11 pages).
(Continued)

*Primary Examiner* — Michael Kornakov
*Assistant Examiner* — Natasha Campbell
(74) *Attorney, Agent, or Firm* — Metz Lewis Brodman Must O'Keefe LLC

(57) ABSTRACT

A device for removing secretions from an artificial tube is provided. The device may include a clearing catheter and a driving mechanism that may apply repetitive motion to the clearing catheter. In another version of the device, the clearing catheter may dispense irrigation fluid and aspirate the irrigation fluid. The clearing catheter may have an irrigation and an aspiration lumen that may both reciprocate
(Continued)

with the clearing catheter. In another version a compliant member into which irrigation fluid is located may be present.

22 Claims, 19 Drawing Sheets

(52) U.S. Cl.
CPC . *A61M 2025/0019* (2013.01); *A61M 2209/10* (2013.01); *B08B 2209/027* (2013.01)

(56) References Cited

U.S. PATENT DOCUMENTS

| | | | |
|---|---|---|---|
| 4,696,296 | A | 9/1987 | Palmer |
| 4,979,939 | A | 12/1990 | Shiber |
| 5,003,657 | A | 4/1991 | Boiteau |
| 5,029,580 | A | 7/1991 | Radford et al. |
| 5,181,908 | A | 1/1993 | Bell |
| 5,220,916 | A | 6/1993 | Russo |
| 5,251,356 | A | 10/1993 | Oaki et al. |
| 5,254,098 | A | 10/1993 | Ulrich et al. |
| 5,277,177 | A | 1/1994 | Page et al. |
| 5,279,549 | A | 1/1994 | Ranford |
| 5,897,534 | A | 4/1999 | Heim et al. |
| 5,902,314 | A | 5/1999 | Koch |
| 6,047,431 | A | 4/2000 | Canonica |
| 6,082,361 | A | 7/2000 | Morejon |
| 6,575,944 | B1 * | 6/2003 | McNary ............ A61M 16/0463 128/200.26 |
| 6,725,492 | B2 | 4/2004 | Moore |
| 7,051,737 | B2 | 5/2006 | Kolobow et al. |
| 7,478,636 | B2 | 1/2009 | Madsen et al. |
| 7,581,541 | B2 | 9/2009 | Madsen et al. |
| 7,918,870 | B2 | 4/2011 | Kugler et al. |
| 7,938,819 | B2 | 5/2011 | Kugler et al. |
| 8,025,655 | B2 | 9/2011 | Kugler et al. |
| 8,083,727 | B2 | 12/2011 | Kugler et al. |
| 8,157,919 | B2 | 4/2012 | Vazales et al. |
| 8,381,345 | B2 | 2/2013 | Vazales et al. |
| 8,382,908 | B2 | 2/2013 | Vazales et al. |
| 8,458,844 | B2 | 6/2013 | Vazales et al. |
| 8,468,637 | B2 | 6/2013 | Vazales et al. |
| 8,534,287 | B2 | 9/2013 | Vazales et al. |
| 8,601,633 | B2 | 12/2013 | Vazales et al. |
| 9,095,286 | B2 | 8/2015 | Vazales et al. |
| 2002/0069893 | A1 | 6/2002 | Kawazoe |
| 2002/0099387 | A1 | 7/2002 | Gauderer et al. |
| 2003/0181876 | A1 | 9/2003 | Ahn et al. |
| 2003/0181934 | A1 | 9/2003 | Johnston et al. |
| 2003/0209258 | A1 | 11/2003 | Morejon |
| 2004/0181194 | A1 | 9/2004 | Perkins |
| 2006/0276743 | A1 | 12/2006 | MacMahon et al. |
| 2007/0038158 | A1 * | 2/2007 | Nita ................ A61B 17/22012 601/2 |
| 2007/0093779 | A1 | 4/2007 | Kugler et al. |
| 2007/0093780 | A1 | 4/2007 | Kugler et al. |
| 2007/0093781 | A1 | 4/2007 | Kugler et al. |
| 2007/0093782 | A1 | 4/2007 | Kugler et al. |
| 2007/0093783 | A1 | 4/2007 | Kugler et al. |
| 2007/0225615 | A1 | 9/2007 | Chechelski et al. |
| 2007/0244423 | A1 | 10/2007 | Zumeris et al. |
| 2009/0188531 | A1 | 7/2009 | Boyle |
| 2009/0264833 | A1 | 10/2009 | Boyle, Jr. |
| 2011/0106019 | A1 | 5/2011 | Bagwell et al. |
| 2011/0276079 | A1 | 11/2011 | Kugler et al. |
| 2012/0016272 | A1 | 1/2012 | Nita et al. |
| 2012/0071854 | A1 | 3/2012 | Kugler et al. |
| 2012/0136382 | A1 | 5/2012 | Kugler et al. |

FOREIGN PATENT DOCUMENTS

| | | |
|---|---|---|
| WO | WO 2004098654 A2 | 11/2004 |
| WO | WO 2007033052 | 3/2007 |
| WO | WO2011126812 A2 | 10/2011 |

OTHER PUBLICATIONS

United States Patent and Trademark Office; Office Action Summary; U.S. Appl. No. 14/182,088; Sep. 11, 2014; pp. 1-17; publisher United States Patent and Trademark Office, Alexandria, Virginia, USA; copyright and mailing date Sep. 11, 2014; copy enclosed (17 pages).

* cited by examiner

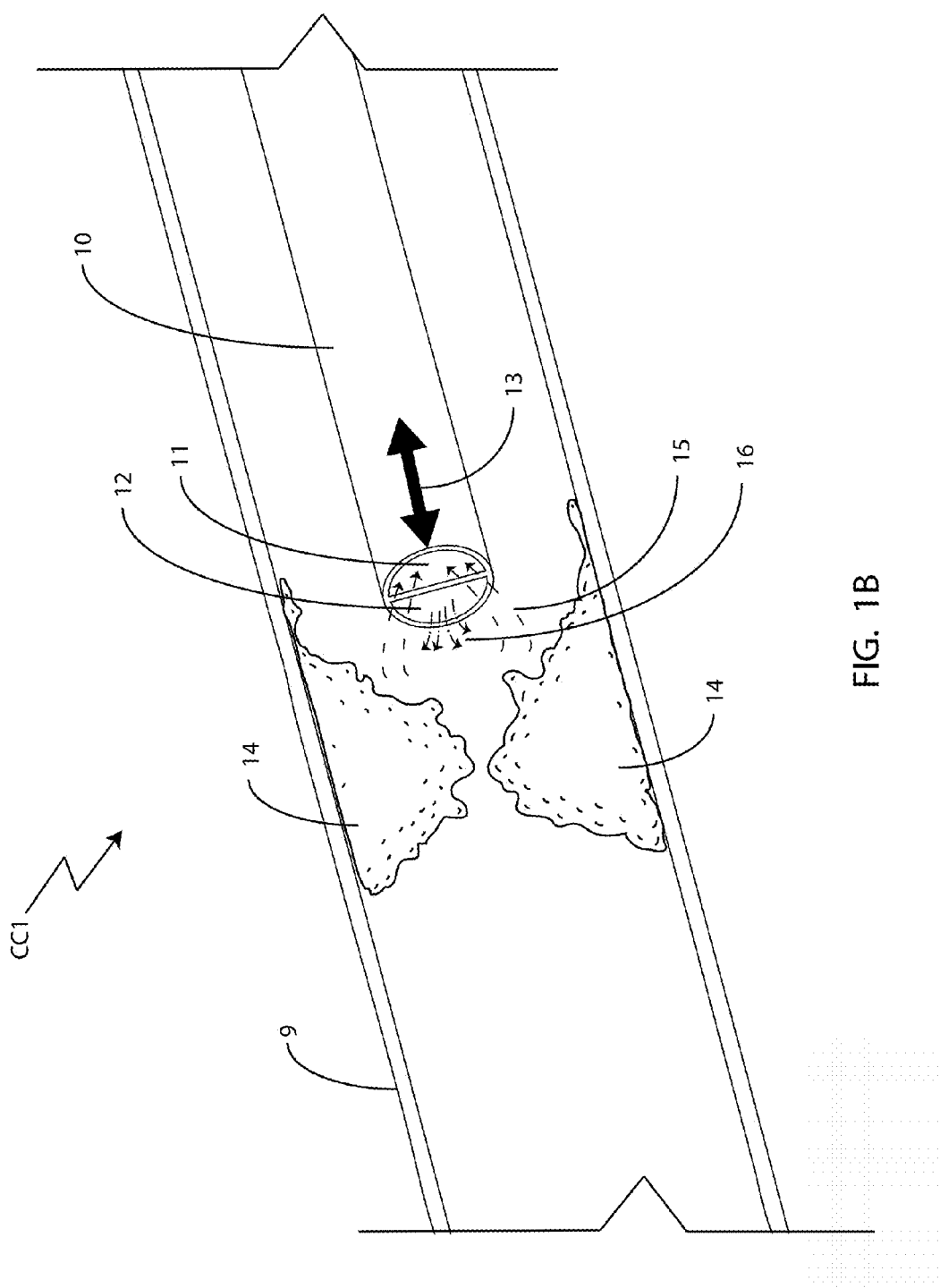

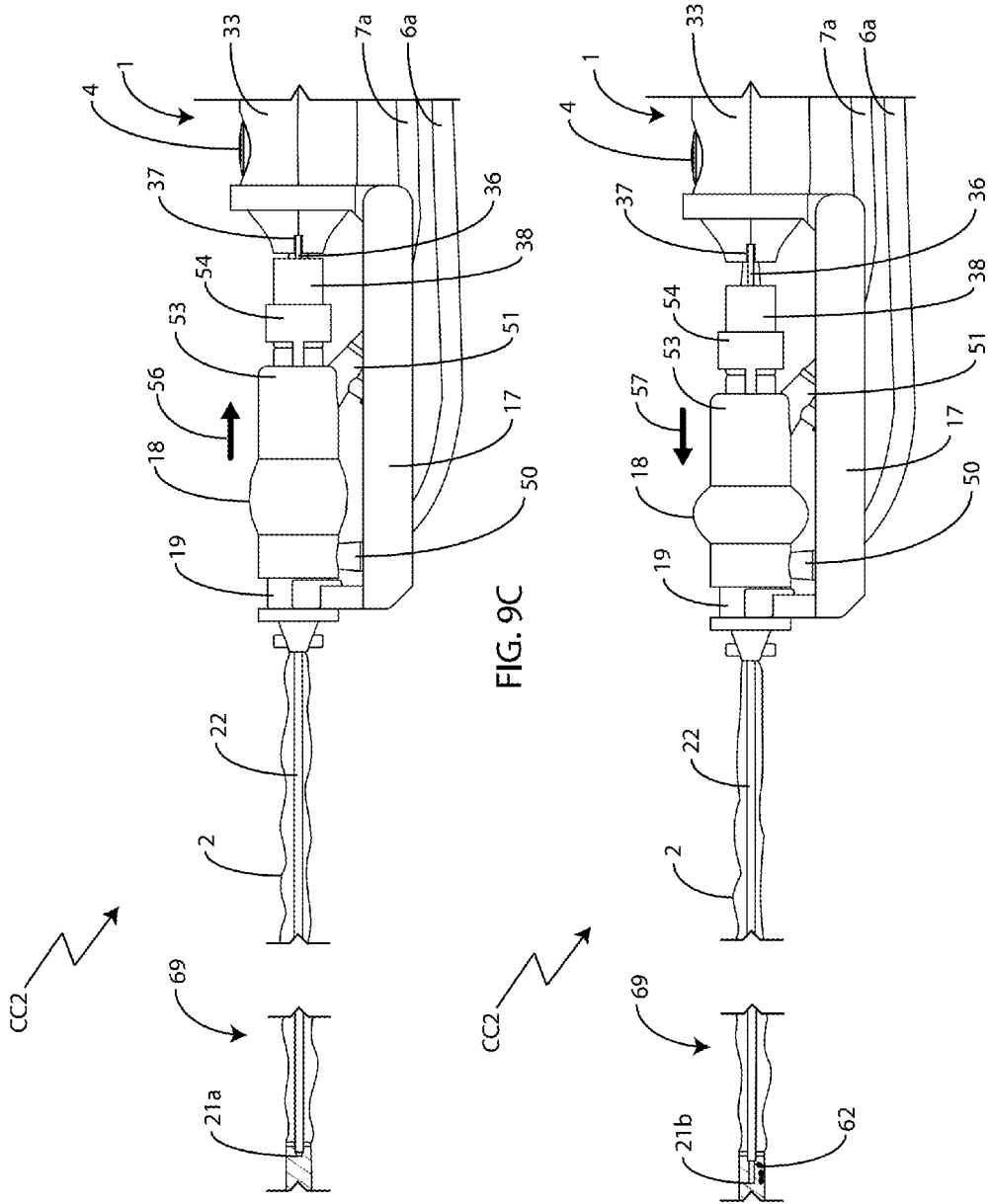

ACTIVE SYSTEM FOR IN-SITU CLEARING OF SECRETIONS AND OCCLUSIONS IN TUBES

CROSS REFERENCE TO RELATED APPLICATIONS

This patent application claims priority to U.S. Patent Application Ser. No. 61/712,437, filed Oct. 11, 2012 entitled Pediatric Endotracheal Tube Clearing System and all of whose entire disclosures are incorporated by reference herein in their entirety for all purposes.

STATEMENT REGARDING FEDERALLY SPONSORED RESEARCH OR DEVELOPMENT

This invention was made with government support under IIP-0810029 and IIP-0923861 awarded by the National Science Foundation, and 1R43HD074310-01A1 awarded by the National Institutes Of Health. The government has certain rights in the invention.

BACKGROUND OF THE INVENTION

1. Field of the Invention

The present invention pertains generally to the field of medical devices, and more specifically to a system for in-situ clearing of secretions in endotracheal tubes and other tubes in the body where secretions or other materials accumulate and negatively impact tube patency.

2. Background

The following is a description of the background of endotracheal tubes (ETTs). It should be understood that the device and method of the present invention is not limited to the clearing of ETTs but is applicable to a range of artificial tubes such as indwelling catheters, pigtail catheters, abscess drains, and chest tubes and that ETTs are being discussed simply by way of example. It should also be understood that the device and method of the present invention is not limited to secretions but is applicable to a range of accumulating and/or occluding materials such as blood, clots, and ingrown tissues/membranes.

Automated mechanical ventilation is often required for patients under anesthesia and for longer-term breathing assistance in compromised patients. Endotracheal tubes are placed in the upper respiratory tract of patients to provide direct airway access when connected to a mechanical ventilator. Annually, 50 million ETTs are sold globally. Patients intubated with ETTs are unable to effectively clear lung secretions, and therefore secretions can accumulate and partially occlude the inside of the ETT. This leads to increased airway resistance and a potentially negative impact on patient health if not remedied. Without proper air humidification, the secretions also potentially become dried, thick, and difficult to remove.

The most routine method to maintain ETT patency is periodic aspiration with a suction catheter. The suction catheter is designed to be momentarily inserted down the ETT manually while attached to a negative pressure source. There are two general types of suction catheters: open and closed. An open suction catheter requires the patient to be disconnected from the ventilator for the suctioning procedure. A closed suction catheter is enclosed in a sterility sleeve and remains attached to the ventilator circuit the entire time. Suctioning can occur without having to shut off the ventilator or disconnect the patient. Whether open or closed, the general suction procedure remains the same. With one hand stabilizing the proximal end of the ETT, the suction catheter is fed into the ETT with the opposite hand until the end is reached, being careful to not over-insert the catheter beyond the tip of the ETT. While retracting the suction catheter, the negative pressure is applied to suction out secretions accumulated on the inner wall of the ETT. It is generally desired for the entire suction procedure to be performed in 10-15 seconds, or $\leq 5$ seconds in children to minimize the impact of the suctioning procedure on lung mechanics and respiration. Generally, a patient will require suctioning every 4-6 hours, but the process may be performed with greater regularity if necessary. The procedure is recommended on an as needed basis, not a regular interval, due to the detrimental effect on the patient.

Attempts to clear the ETT using standard techniques are often ineffective, time-consuming, expensive, and an agonizing experience for the patients, families, and health care providers. Standard methods can also dislodge bacteria-containing particles into the lungs. Ventilator Acquired Pneumonia (VAP) is a major source of infection in hospitals, and is often due to the direct path to the lungs for bacteria from ETT intubation. Standard suctioning has an effect on lung mechanics, including decreased expired tidal volume and lung compliance. Clinical side effects include hypoxia (low oxygen in blood), bradycardia (low heart rate), or atelectasis (collapse of part of the lung). In general, the long term effects of acute changes in lung mechanics or cumulative exposures to short term clinical side effects of suctioning on long term respiratory health is not known. Minimizing the potential negative impacts of the suctioning process on the lungs is desirable.

Negative effects can be minimized with use of smaller diameter suction catheters, which allow improved airflow during suctioning. With narrow ETTs (such as neonatal or pediatric patients) this is difficult to achieve without severely limiting secretion aspiration effectiveness using standard methods. Such small diameter suction catheters may easily clog, depending on the consistency of the secretions. In addition to airflow considerations, larger suction catheters may be difficult to insert if the catheter diameter to ETT inner diameter ratio is larger than 0.7.

Occasionally, physiologic saline is first instilled at the inlet to the ETT in an attempt to hydrate and thin the secretions to encourage its removal during the subsequent suctioning procedure, although this point remains controversial. Additional goals of saline instillation may include lubricating and easing the insertion of the catheter itself, and/or elicitation of a cough from the patient to aid secretion removal. The current methods of instilling saline into ETTs are not precise and there is risk of excess fluid entering the lungs and possibly causing dispersion of adherent contaminating material. Reports further suggest saline instillation may cause greater blood oxygen desaturation than suctioning without saline. Despite lack of evidence supporting saline instillation and its potential risks, many clinicians continue the practice.

When suctioning is unable to restore patency quickly, the only recourse is to replace the ETT, further raising the risk of VAP while also depriving the patient of oxygen until the patient is reintubated and reconnected to the ventilator. The present active device will safely and quickly clear ETTs, while reducing the negative impact the suction procedure has on the lung mechanics of an already compromised patient.

The present device is also applicable to clearing other types of tubes that may become occluded by secretions or other accumulating or occluding material. For example, pigtail catheters for chest drainage may be cleared in the same way.

BRIEF SUMMARY OF THE INVENTION

These and other features are described in or are apparent from the following detailed description of various exemplary embodiments.

It is hereby noted that the term "in situ" is defined as performing an act on an element while the element is being utilized for its commonly known function. For example, per-forming the act of clearing bodily fluids from an ETT in situ refers to clearing a clog or blockage in an ETT while the tube is dwelling within the trachea of a living being, human or other.

The device may be a reusable handset coupled to a disposable clearing catheter that work together to clear secretions from ETTs and other tubes in the body more quickly, thoroughly, and with less impact on the patient's lungs or other organs than any current method. The clearing catheter may be designed to operate within a closed system, meaning that the connection to and function of the ventilator is not interrupted when secretion clearing is conducted. Gentle oscillation motion may be applied to the clearing catheter by the handset.

The clearing catheter may consist of a dual lumen with distal delivery of low volume, continuous irrigation balanced with aspiration—allowing secretions to be broken up and aspirated, without any fluid or debris passing the distal end of the endotracheal tube. Vibration may aid the break-up of tough secretions, allows easier insertion (less hang up in tube), and prevents secretions from getting stuck in the catheter. Implementing the motion applied to the clearing catheter, along with the irrigation and suction, while maintaining the closed system, may require the use of custom connections.

A method is also disclosed for the in situ clearing of accumulations or occlusions in artificial tubes (e.g., ETT tubes, chest tubes, pigtail tubes, abscess drains) completely or partially disposed within a living being. The method comprises: coupling a first end of a releasably-securable flexible clearing member to a driving mechanism where the driving mechanism remains outside of the living being; and the second working end of the flexible clearing member is disposed inside a closed system in communication with the interior of the artificial tube; and energizing the driving mechanism such that the flexible clearing member experiences repetitive motion and positioning the flexible clearing catheter such that the second working end of the flexible clearing catheter comes into repetitive contact with the accumulation or occlusion for clearing the accumulation or occlusion therein; and wherein the flexible clearing catheter moistens and clears the dried or viscous accumulations or occlusions when positioned within a straight portion or within a curved portion of the artificial tube, with minimal effect on the original function of the artificial tube in the patient.

BRIEF DESCRIPTION OF SEVERAL VIEWS OF THE DRAWINGS

A full and enabling disclosure of the present invention, including the best mode thereof, directed to one of ordinary skill in the art, is set forth more particularly in the remainder of the specification, which makes reference to the appended Figures in which:

FIG. 1B illustrates a close-up view showing the fundamental mechanisms of clearing action at the distal tip of the clearing catheter of the system presented in FIG. 1A.

FIGS. 9C and 9D illustrates the extents of motion of the inflatable compliant reservoir-based pump shown in FIG. 9A.

Figure 1:
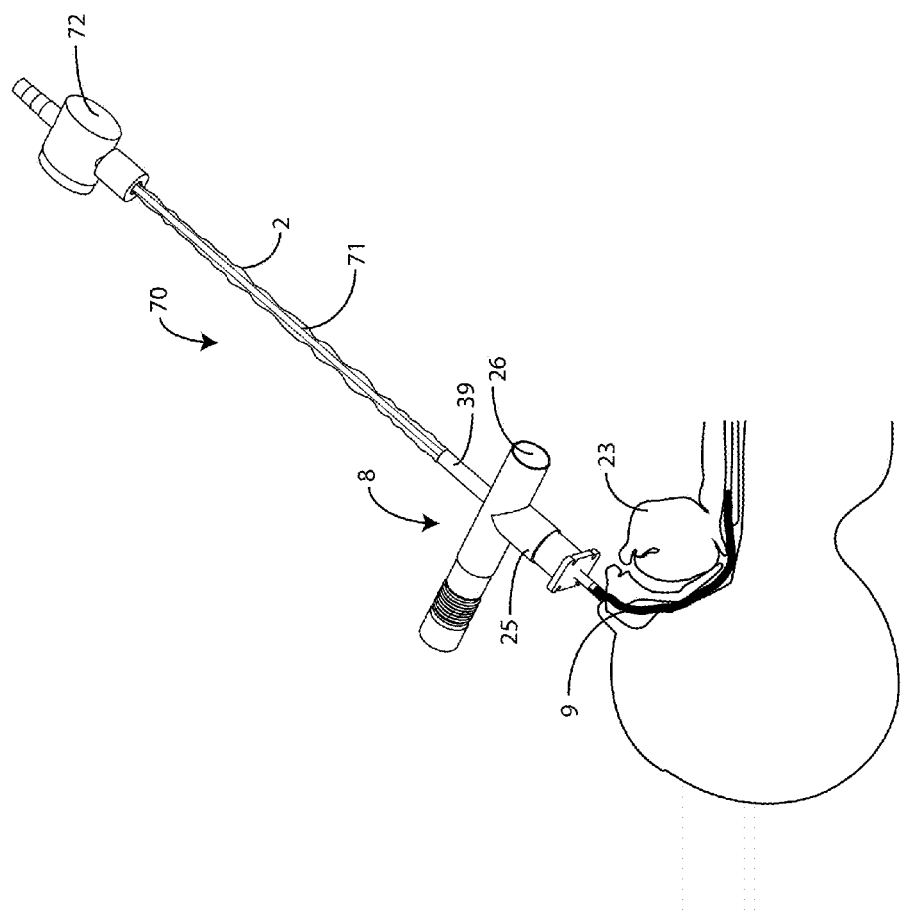
FIG. 1 illustrates arrangement of a standard closed suction catheter system attached to a ventilator circuit of an intubated patient (PRIOR ART).

Repeat use of reference characters in the present specification and drawings is intended to represent the same or analogous features or elements of the invention.

REFERENCE LABELS

CC1 Split Lumen Clearing Catheter
CC2 Sheathed Clearing Catheter
1 Handset
2 Sterility Sleeve
3 Catheter Adapter

REFERENCE LABELS

4 Power Button
5 Power Cable
6a Irrigation Tubing
6b Irrigation Connector
6c Irrigation Catheter Coupler
7a Aspiration Tubing
7b Aspiration Connector
7c Aspiration Catheter Coupler
8 Clearing Catheter Coupler
9 Endotracheal Tube (ETT)
10 Clearing Catheter
11 Aspiration Lumen
12 Irrigation Lumen
13 Oscillation
14 Secretions
15 Aspiration Flow
16 Irrigation Flow
17 Bracket
18 Compliant Wall
19 Bracket Adapter
20 Sheathed Clearing Catheter
21 Inner Clearing Catheter
21a Inner Clearing Catheter Retracted
21b Inner Clearing Catheter Extended
22 Outer Sheath
23 Patient
24 Ventilator Port
25 ETT Port
26 Additional Port
27 Voice Coil
28a Magnet Assembly
28b Opposite Magnet Assembly
29 End Cap
30 Bearing
31 Shaft
32 Shaft Guides
33 Handset Housing
34 VCM (voice coil motor) Body
35 Pole Piece
36 Keys
37 Keyway
38 Keyed Coupler
39 Clearing Catheter Port
40 Centering Magnet
41 VCM
42 Dual Lumen Connector
43 Male Component
44 Female Component
45 Inline Dual Lumen Connector
46 Closed System Adapter
47 Syringe
48 Plunger
49 Syringe Body
50 Irrigation Port
51 Aspiration Port
52 Compliant Reservoir
53 Compliant Reservoir Adapter
54 Magnetic Adapter
55 Magnet
56 Retracted
57 Extended
58 Peristaltic Pump
59 Pump Tubing
60 Fluid Reservoir
61 Pump Housing
62 Irrigating Droplets
63 Syringe Coupling Bracket
64 Clearing Catheter Magnet
65 IV Pole
66 Pressure Data
67 Current Embodiment
68 Standard 5 Fr Suction Catheter
69 Closed Clearing Catheter System
70 Standard Closed System
71 Suction Catheter
72 Suction Valve
73 Brush

REFERENCE LABELS

74 Irrigation Port Valve
75 Irrigation Seal
76 Irrigation Valve

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations. The preferred embodiments are illustrated in FIGS. 1A-11 with the numerals referring to like and corresponding parts.

The present devices and methods may effectively remove accumulated secretions, blood, clots, or ingrown tissue/membranes from the internal portions of an artificial tube, and preferably an ETT, including pediatric and neonatal ETT. The action of removing accumulated secretions, blood, clots, or ingrown tissue/membranes can also be referred to as a "maintenance action".

A reusable handset may be provided that is releasably coupled to a disposable clearing catheter that work together to clear secretions from ETTs and other tubes in the body more quickly, thoroughly, and with less impact on the patient's lungs or other organs than any current method. The clearing catheter may be designed to operate within a closed system, meaning that the path to and function of the ventilator is not interrupted when secretion clearing is conducted. Gentle oscillatory motion maybe applied to the clearing catheter by the handset.

In addition, the clearing catheter embodiments themselves as they are described here may work relatively effectively, though less preferably, without being attached to a driving mechanism and without experiencing repetitive motion. In this case, the advantage over standard suction catheters is the incorporation of multiple lumens, enabling simultaneous irrigation and aspiration.

The clearing catheter consists of multiple lumens with distal delivery of low volume, continuous irrigation balanced with aspiration in separate lumens—allowing secretions to be broken up and aspirated, without any fluid or debris passing the distal end of the ETT. Vibration aids the break-up of tough secretions, allows easier insertion (less hang up in tube), and prevents secretions from getting stuck in the catheter. Implementing the motion applied to the clearing catheter, along with the irrigation and suction, while maintaining the closed system, may require, in some instances, the use of custom connections.

As used herein, the distal direction is the direction toward the patient and away from the health care provider. The proximal direction is toward the health care provider and away from the patient.

FIG. 1 illustrates the basic setup of an ETT with a standard closed system 70 and a suction catheter 71 installed within.

The suction catheter 71 is designed to be momentarily inserted down the ETT 9 manually while attached to a negative pressure source. There are two general types of suction catheters: open and closed. An open suction catheter requires the patient to be disconnected from the ventilator for the suctioning procedure. A standard closed system 70 is enclosed in a sterility sleeve 2 and remains attached to the ventilator circuit the entire time. Suctioning can occur without having to shut off the ventilator or disconnect the patient. A slip fitting (not shown) within the clearing catheter coupler 8 enables the catheter to insert into the ETT 9 while a seal is constantly maintained to keep the interior of the sterility sleeve 2, from inflating/deflating and shunting air away from lungs during ventilation cycle. Whether open or closed, the general suction procedure remains the same. With one hand stabilizing the proximal end of the ETT 9, the suction catheter 71 is fed into the ETT 9 with the opposite hand until the end is reached, being careful to not over-insert the suction catheter 71 beyond the tip of the ETT 9. While retracting the suction catheter 71, the negative pressure is applied to suction out secretions 14 accumulated on the inner wall of the ETT 9. It is generally desired for the entire suction procedure to be performed in 10-15 seconds, or ≤5 seconds in children to minimize the impact of the suctioning procedure on lung mechanics and respiration.

Presently, the new clearing catheter designs (10 and 20) may be contained, as with a conventional suction catheter 71, within a closed clearing catheter system 69. A handset 1 is releasably connected to the clearing catheters (10 or 20) which may apply gentle mechanical action along with irrigation flow and suction.

Figure 1A:
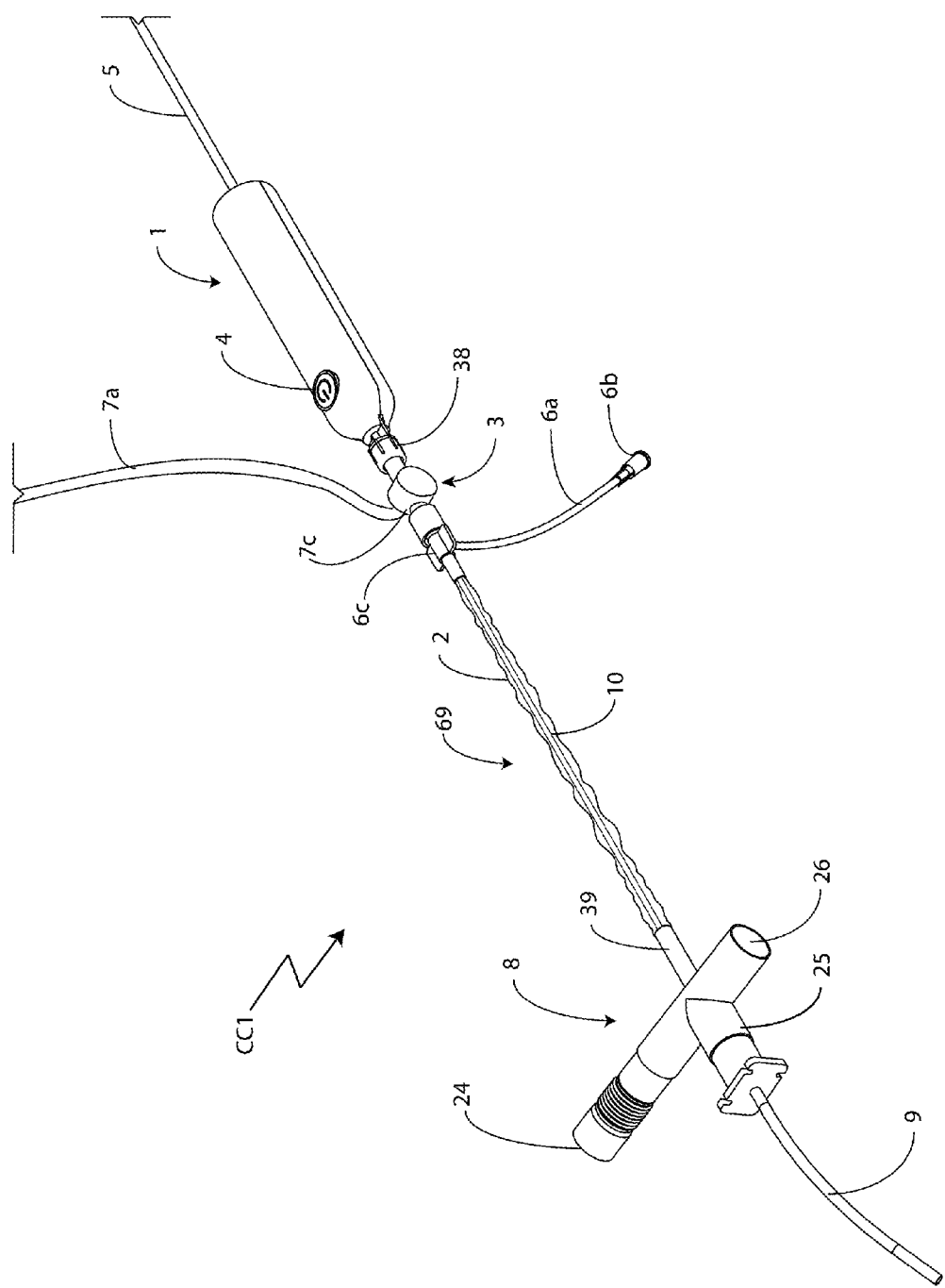
FIG. 1A illustrates the basic components of an active clearing catheter system to remove secretions from ETTs in-situ.
Figure 2A:
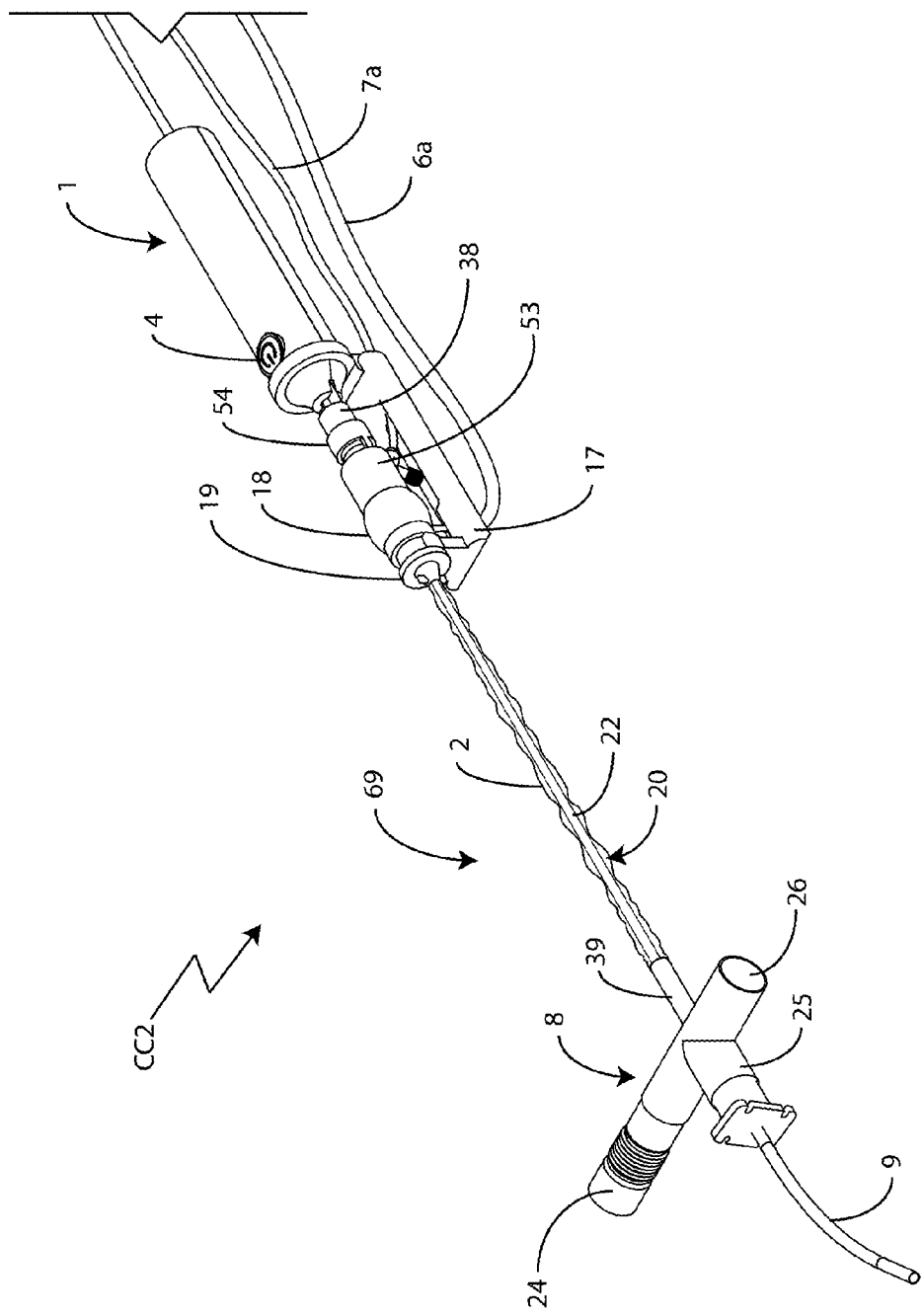
FIG. 2A illustrates the basic components of an active clearing catheter system to remove secretions from endotracheal tubes in-situ, in which the clearing catheter of the device contains a separate outer sheath which does not undergo repetitive motion.

FIGS. 1A and 2A illustrates the basic components of the handset 1 and closed clearing catheter system 69 designed to remove secretions 14 (not shown) from endotracheal tubes (ETT) more effectively and with less negative effect on the patient's lungs. The system together consists of a clearing catheter (e.g. 10 or 20) contained in a closed clearing catheter system 69 and a handset 1 may apply repetitive motion to the clearing catheter (e.g. 10 or 20) or may not apply repetitive motion to the clearing catheter (e.g. 10 or 20). The handset 1 could also be envisioned as a control box that instead rests on a surface, leaving both hands of the clinician free. The clearing catheter (e.g. 10 or 20) passes through an attached clearing catheter coupler 8 (i.e. "T", "Y", or straight coupling). Opposite the clearing catheter (e.g. 10 or 20) is a tube 9, such as an endotracheal tube (ETT). In the illustrations, an ETT is shown, although the invention is not limited in application to the ETT. A ventilator is attached to the ventilator port 24. On the additional port 26 of the fitting, if present, a separate device may be attached for other medical treatments. The purpose of the closed system 69 is to maintain sterility and to avoid interfering with the primary function of the ETT 9 while secretions 14 (not shown) are being cleared from the ETT 9.

As will be discussed in detail later, there are basically two types of tube clearing catheters disclosed herein, both of which are mechanical tube clearers, which benefit from irrigation and aspiration functions. Both approaches may be enclosed within a closed system. Both approaches may apply gentle oscillatory motion or, though less preferably, may not apply gentle oscillatory motion.

Clearing Catheter Design 1 (CC1) uses a dual lumen connected at the proximal end where the handset 1 may provide mechanical oscillation to both lumens. Oscillation may be back and forth repetitive motion along a longitudinal axis of the clearing catheter, driving mechanism or artificial tube.

Clearing Catheter Design 2 (CC2) uses two separate lumens that may experience relative movement in the longitudinal axis. The inner lumen is connected to the handset 1 which may provide mechanical oscillation. Oscillation may be back and forth repetitive motion along a longitudinal axis of the clearing catheter, driving mechanism or artificial tube. The outer lumen in this case is fixed in position by a bracket which is anchored to the outside of the handset 1. The inner lumen in this case moves freely within the outer lumen, with its distal tip exiting and reentering the distal end of the outer lumen.

Applies to Clearing Catheter Design 1 (Split Lumen Clearing Catheter)

FIGS. 1A and 1B illustrate in more detail the components of the clearing catheter design 1 CC 1 where the clearing catheter 10 may be an oscillating dual lumen or, less preferably, may be a non-oscillating dual lumen. The clearing catheter 10 passes through an attached clearing catheter coupler 8 (i.e. "T", "Y", or straight coupling) (shown in FIG. 1A). Opposite the clearing catheter is a tube 9, such as an endotracheal tube (ETT). The purpose of the closed system 69 is to avoid interfering with the primary function of the ETT 9 while secretions 14 (shown in FIG. 1B) are being cleared from the ETT 9.

Figure 7:
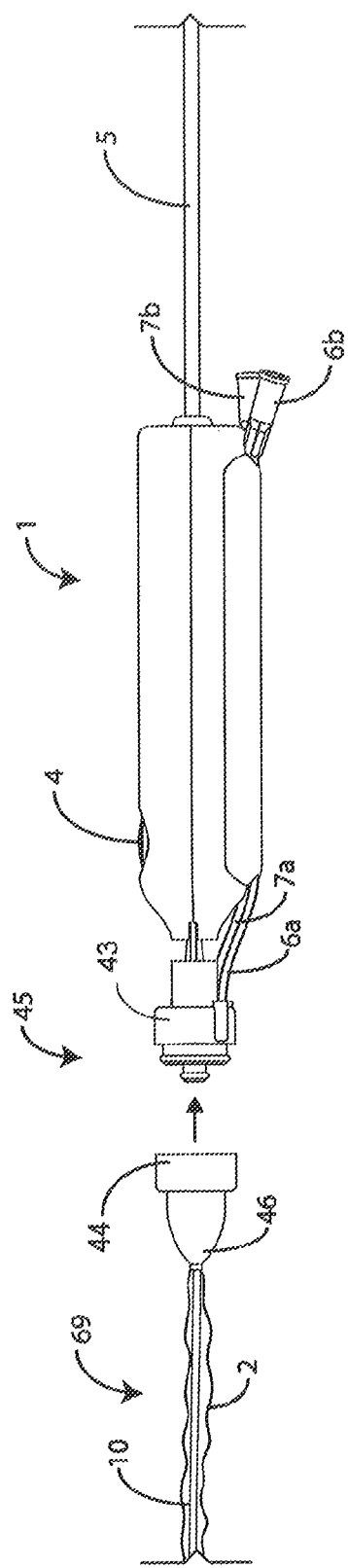
FIG. 7 shows the use of an inline dual lumen connector to simplify the fluid and closed system connections of the active system.

A multi-port catheter adapter 3 (shown in FIG. 1A and in cross-sectional view in FIG. 3C) on the proximal end of the clearing catheter 10 may connect to a handset 1 (shown in FIG. 1A) via a keyed coupler 38 (shown in FIG. 1A) which may provide mechanical oscillation 13 (shown in FIG. 1B) in a frequency range of 1-500 Hz, but preferably 50-150 Hz. The oscillations 13 have a stroke length of 0.05-3.0 mm, but preferably 0.25-1.0 mm at the distal tip of the clearing catheter 10. Compliant tubing, such as silicone, may be used to link the irrigation catheter coupler 6c to a fluid source via irrigation tube 6a (shown in FIG. 1A) as well as link the aspiration catheter coupler 7c to a suction source via aspiration tubing 7a (shown in FIG. 1A), thus permitting both an irrigation flow 16 (shown in FIG. 1B) of fluid, preferably saline, from an irrigation lumen 12 (shown in FIG. 1B) and aspiration flow 15 (shown in FIG. 1B) (suction) of the secretions 14 through an aspiration lumen 11 (shown in FIG. 1B) in the clearing catheter 10. The irrigation and aspiration tubing (6a and 7a, respectively) are sufficiently compliant so as to allow the more rigid catheter adapter 3 (which includes the irrigation catheter coupler 6c and aspiration catheter coupler 7c) and attached clearing catheter 10 to freely oscillate when handset 1 is actuated, even when distal portion of the tubing (6a and 7a) is anchored to the handset 1 (such as shown in FIG. 7). The sterility sleeve 2 (shown in FIG. 1A) is composed of relatively thin and flexible material such as plastic which easily folds as the clearing catheter inserts into the tube 9, therefore very little if any vibration is transferred down the distal end of the sterility sleeve 2. As shown in more detail in FIG. 1B, the mechanical oscillations 13 combined with the irrigation flow 16, assist in thinning and breaking up the secretions 14 present in the tube 9, such as an ETT.

Figure 1C:
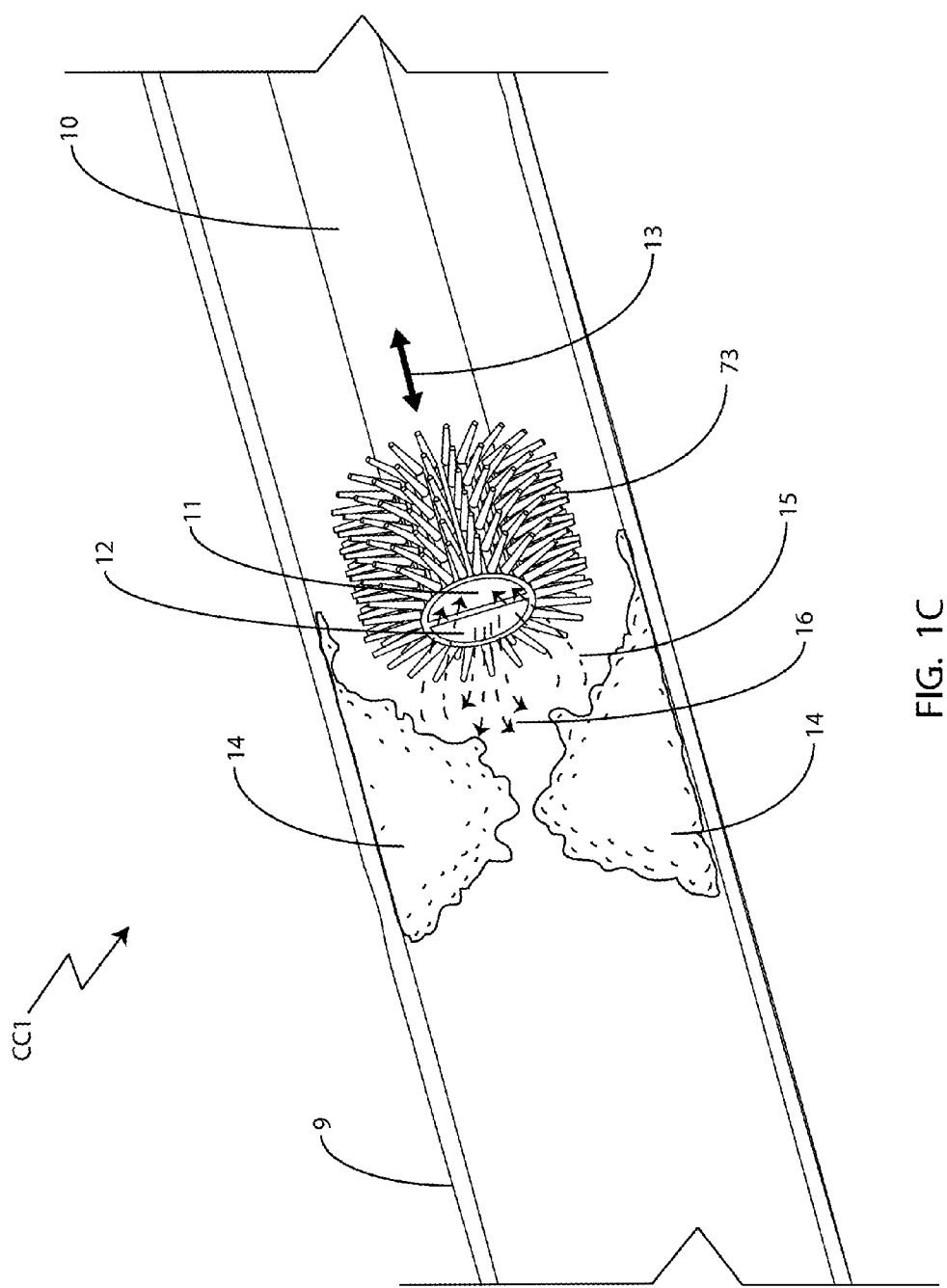
FIG. 1C illustrates a close-up view showing the fundamental mechanism of clearing action at the distal tip of the clearing catheter with brush tip of the system presented in FIG. 1A.

FIG. 1C illustrates an alternate embodiment of clearing catheter design 1 CC1, in which a brush 73 is located at the distal end of the clearing catheter 10. The brush 73, being securely connected to the clearing catheter 10, may oscillate 13 with it. The oscillation 13 motion of the brush 73 further assists in breaking up secretions 14 which may be adherent to the inner walls of the ETT 9. This alternative embodiment may also be used without oscillation, thereby using irrigation and aspiration along with the brush to clear secretions 14.

Figure 6:
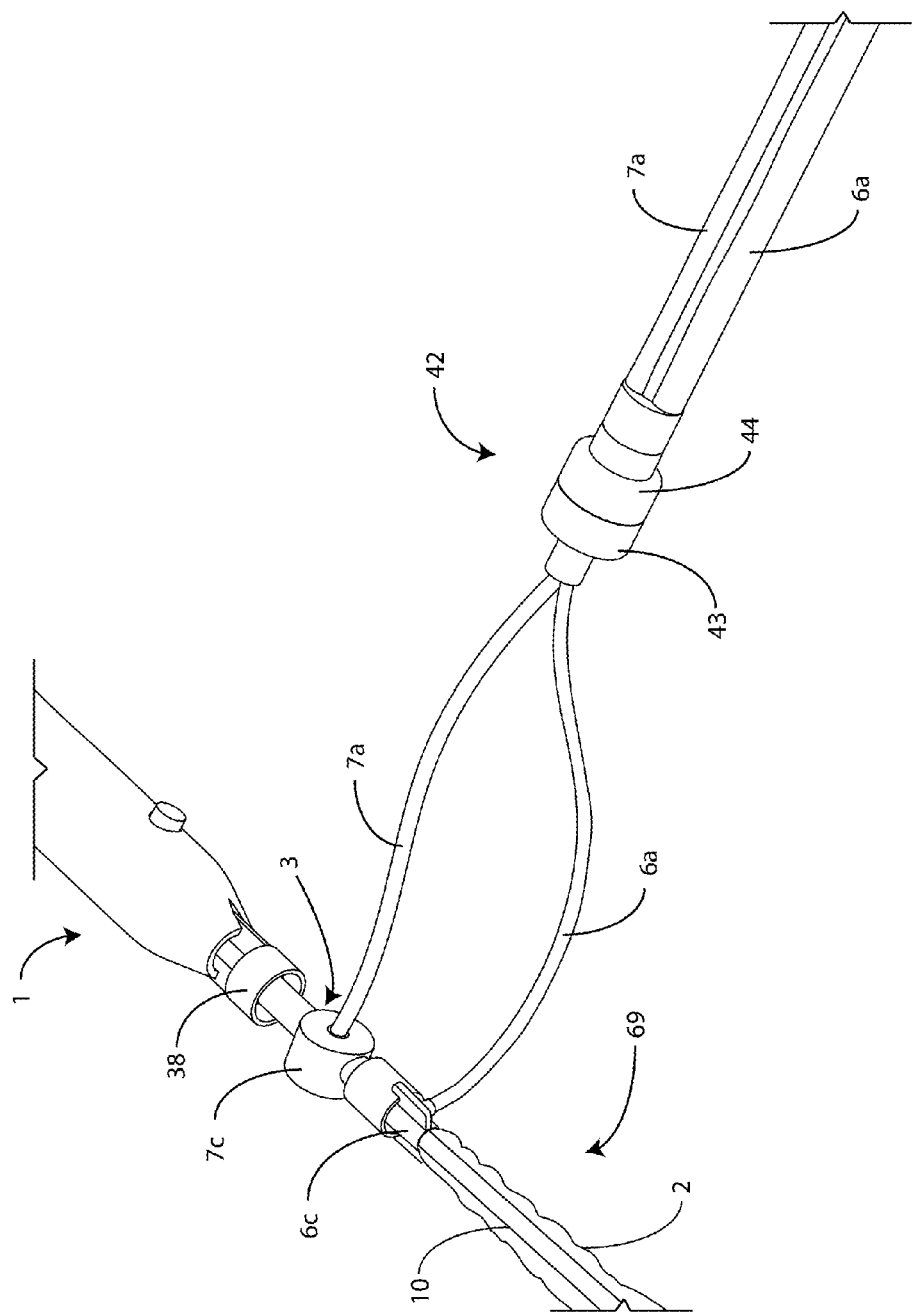
FIG. 6 shows the use of a dual lumen connector to simplify the fluid connections to the adapter of clearing catheter.

FIG. 6 and FIG. 7 refer to methods of making the connections between the clearing stem and the irrigation/ aspiration sources. Illustrations are specific to the split lumen clearing catheter design CC1 but the basic connections could be adapted to the sheathed clearing catheter design CC2 (see below) with minor modification. Since the device requires multiple connections, novel methods of simplifying the connections for the operator are of value. As shown in FIG. 6, the irrigation tubing 6a which provides irrigation function, connects to the clearing catheter adapter 3 by an irrigation catheter coupler 6c. Similarly, the aspiration tubing 7a which provides aspiration function, also connects at the clearing catheter adapter 3 by an aspiration catheter coupler 7c. The ordering of the irrigation catheter coupler 6c and the aspiration coupler 7c of catheter adapter 3 can be reversed. A dual lumen connector 42 which contains a male component 43 and female component 44 and enable quick connection of both the irrigation tubing 6a and aspiration tubing 7a coming from their source (possibly some distance from the patient or more directly coupled to the handset 1) when the device is to be used in a clearing procedure on the patient. When the handset is activated in FIG. 6, the keyed coupler 38, catheter adapter 3 and the attached clearing catheter 10 are mechanically oscillated together. Minimal vibration is transferred to the sterility sleeve 2 (attached to distal end of catheter adapter 3) or the irrigation tubing 6a or aspiration tubing 7a. FIG. 7 refers to a similar connector that is placed in-line with the handset 1 and closed system 69. The in-line configuration facilitates the connection of the irrigation -6b and closed system 69 to the handset 1 at the same time, minimizing the amount of connections the operator has to make in order to use the device. In FIG. 7, the sterility sleeve 2 is connected to a closed system adapter 46, which is part of the female component 44 of the inline dual lumen connector 45. The male component 43 interlocks with the female component 44 of the inline dual lumen connector 45. The male component 43 is connected to the handset 1 in lieu of the catheter adapter 3 on several other configurations. The male component 43 contains ports for irrigation tubing 6a and aspiration tubing 7a, which may be run alongside the handset 1 and terminates in an irrigation connector 6b and an aspiration connector 7b, respectively. Multiple sets of tubing may be used for various functions. The irrigation connector 6b and/or aspiration connector 7b, in this case, may be permanently attached to accessory equipment (i.e., aspiration or irrigation pumps), so that the operator must only make the single connection of the inline dual lumen connector 45 to connect the closed clearing catheter system 69 and its functions. When male component 43 is attached to female component 44 and the handset 1 is activated, both components mechanically oscillate as a single unit along with the clearing catheter 10. Tubing 6a and 7a have sufficient compliance so as to not impede the mechanical oscillation of the inline dual lumen connector 45 or attached clearing catheter 10 during operation.

Applies to Clearing Catheter Design 2 (Sheathed Clearing Catheter)

Figure 2B:
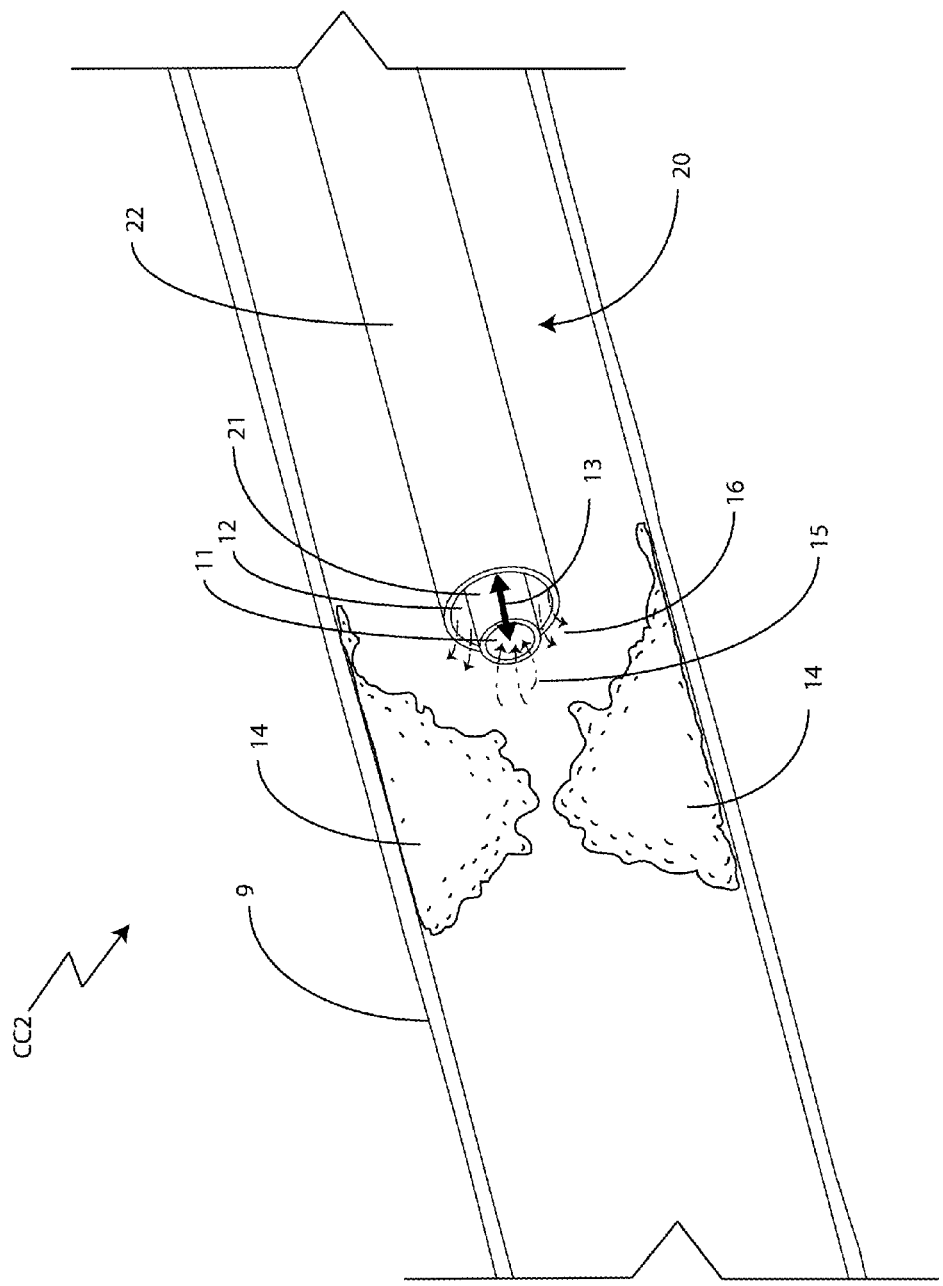
FIG. 2B illustrates a detail view showing the fundamental mechanisms of clearing action of the device in FIG. 2A.

FIGS. 2A and 2B illustrate in more detail the components of the sheathed clearing catheter CC2 which may be an active device to remove secretions 14 (shown in FIG. 2B) from endotracheal tubes 9, in which a sheathed clearing catheter 20 contains an additional non-moving outer sheath 22. The outer sheath 22 is concentrically disposed with regards to an inner clearing catheter 21 (shown in FIG. 2B). The outer sheath 22 does not oscillate and is held stationary by a bracket 17 (shown in FIG. 2A) which is attached to or is integrated into the handset 1 (shown in FIG. 2A). One benefit of this configuration is that the outer sheath 22 may be lightly gripped without damping the oscillation of the inner catheter 21. The inner clearing catheter 21 may be single-lumen in order to accommodate aspiration. As shown in more detail in FIG. 2B, irrigation flow 16 will travel in the space between the outer sheath 22 and the inner clearing catheter 21, this space being referred to as the irrigation lumen 12. The clearing catheter can be reversibly attached to handset 1 by pressing bracket adapter 19 into the bracket 17 and connected the compliant reservoir adapter 53 to the magnet adapter 54 which is attached to the keyed coupler 38. The mechanical oscillations 13 of the compliant reservoir adapter 53 and attached inner clearing catheter 21 combined with the irrigation flow 16, assist in thinning and breaking up the secretions 14 present in the tube 9. Once the secretions 14 are thinned or loosened by the irrigation flow 16 and mechanical oscillation 13, they are removed via aspiration flow 15 through the aspiration lumen 11 in the inner clearing catheter 21. In an alternative, the irrigation flow 16 may work with the aspiration flow 15 to remove secretions 14 without mechanical oscillations, 13. The secretions 14 may be, but not limited to, mucus, blood, clots, or ingrown tissue/membranes. Alternatively, the inner clearing catheter 21 may also be of a multi-lumen design in order to accommodate additional functions.

Figure 9A:
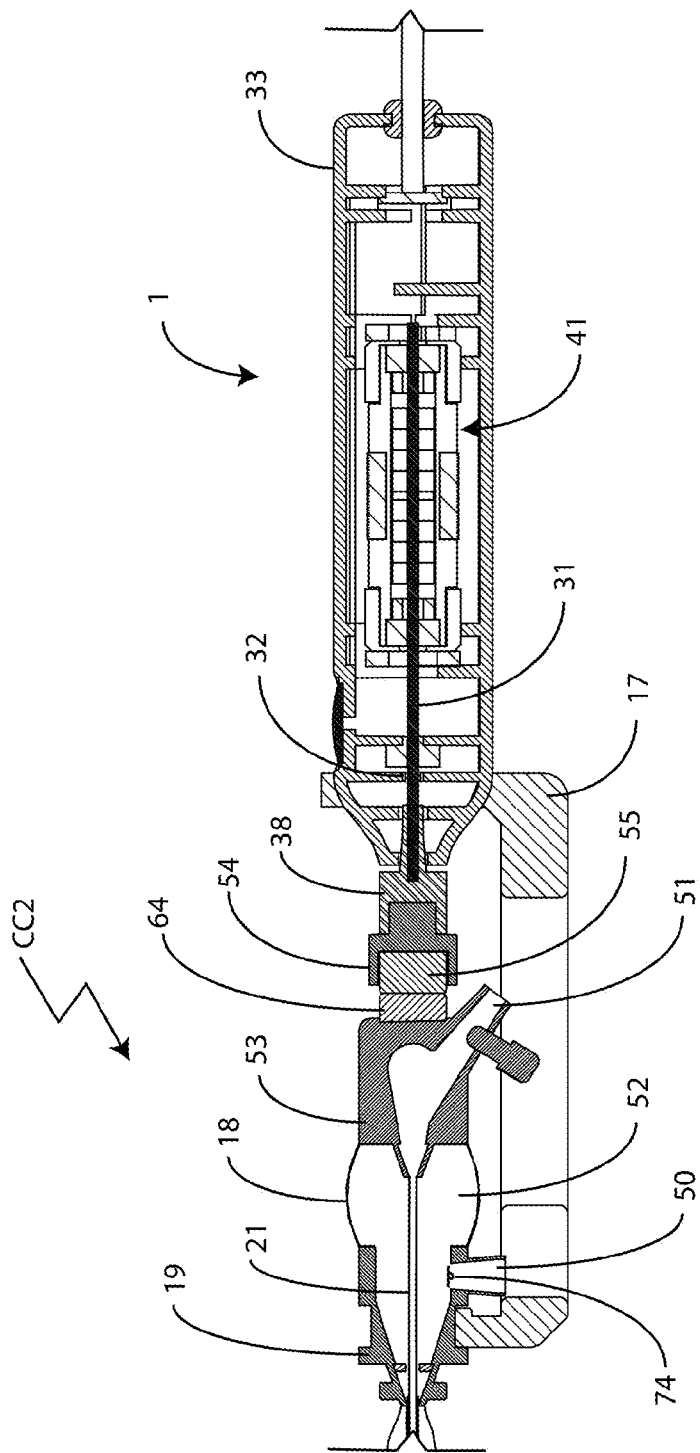
FIG. 9A illustrates the integration of a novel pump based on an inflatable compliant reservoir to both store irrigation fluid and create pressure to drive the irrigation flow.
Figure 9B:
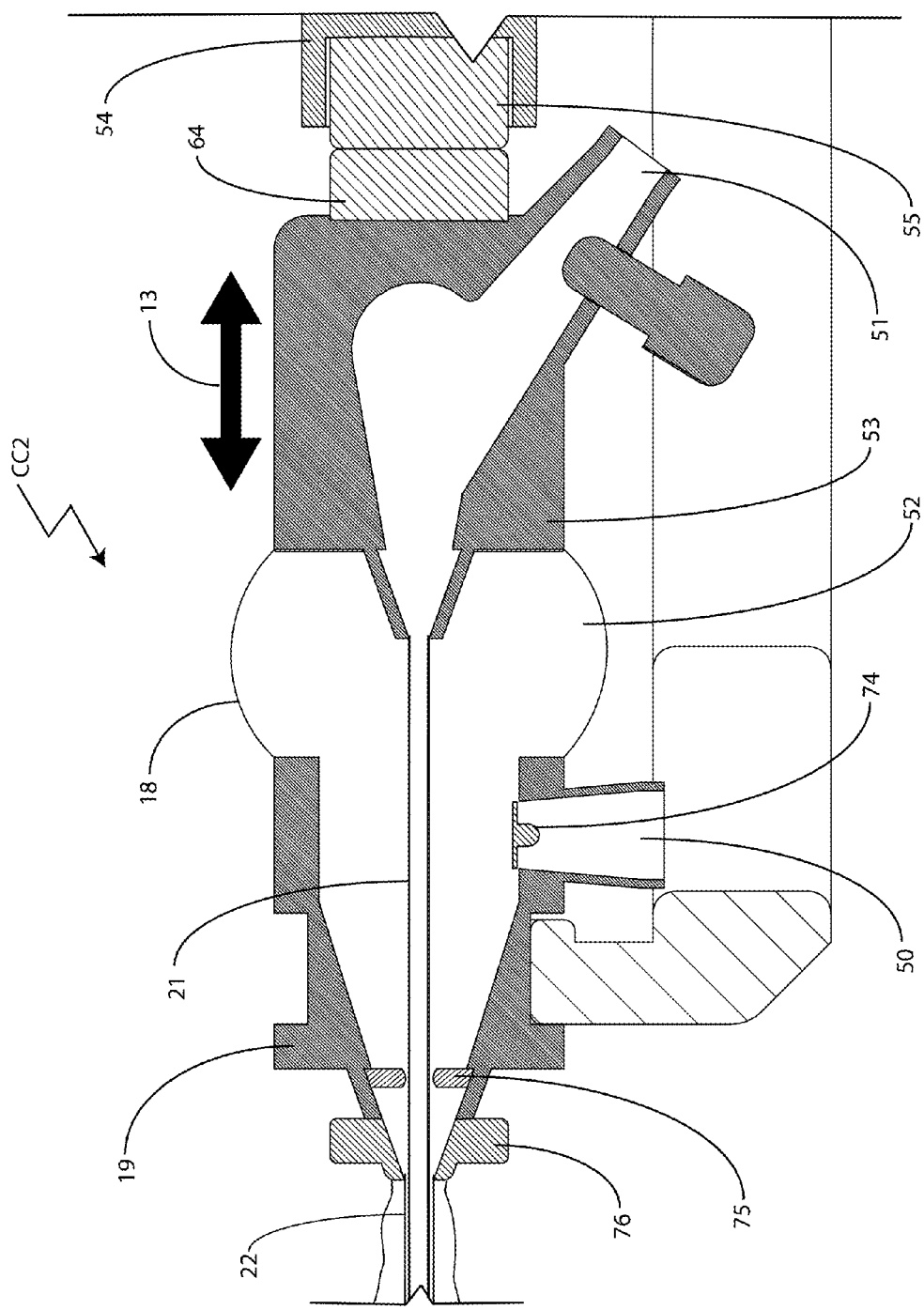
FIG. 9B shows a detailed section view of the components and lumen boundaries which comprise the compliant reservoir-based pump shown in FIG. 9A.

FIG. 9A through FIG. 9D illustrate an embodiment using a compliant reservoir 52 (shown in FIGS. 9A and B) to allow delivery of the irrigation fluid down the irrigation lumen 12 (shown in FIG. 2B) formed between the non-moving outer sheath of 22 and the oscillating inner catheter 21 of the sheathed clearing catheter design CC2. In this embodiment shown in full in FIG. 9A and in detail in FIG. 9B, the shaft 31 is routed through shaft guides 32 and attaches to keyed coupler 38. A magnetic adapter 54 and residing magnet 55 interfaces the keyed coupler 38 with clearing catheter magnet 64. Either magnet 55 or 64 may also be replaced by a magnetically attractive material, such as but not limited to steel. A clearing catheter magnet 64, which is part of the closed clearing catheter system 69, makes the connection with the magnet 55 attached to the handset 1. In order to maintain orientation of the compliant reservoir 52 system and its connections, the magnet 55 and clearing catheter magnet 64, may incorporate a keyway, interlocking feature, unique shape, and/or specific polarization in order to keep the magnets in a stationary position relative to each other when engaged. The magnetic connection may be replaced with some other releasable mechanical mating connection (e.g. slots, dovetail, or snap). Attached to the clearing catheter magnet 64 is a compliant reservoir adapter 53, which includes an aspiration port 51. A compliant reservoir 52 is formed between the compliant reservoir adapter 53 and a bracket adapter 19. A bracket 17 which attaches to the handset 1 is used to secure the bracket adapter 19 and hold it stationary relative to the oscillating inner clearing catheter 21. The bracket adapter 19 contains an irrigation port 50 which is used to pressurize the compliant reservoir 52. Optionally, the irrigation port 50, may incorporate an irrigation port valve 74 (such as a 1-way or 2-way valve) to allow the compliant reservoir 52 to maintain pressure after filling, for instance with a syringe, disposable ampule, or external pump which is only momentarily connected to fill the compliant reservoir 52. In addition, there may be a valve, such as a Tuohy-Borst adapter, that controls the inner diameter of the irrigation seal 75 by tightening or loosening of the irrigation valve 76, thereby reducing or turning off completely the flow of irrigation fluid out of the compliant reservoir 52. When the compliant reservoir adapter 53 is mechanically oscillated along with the inner clearing catheter 21, the compliant wall 18 expands outward to accommodate the fluid that is displaced by the compliant reservoir adapter 53. This produces pressure fluctuation inside the compliant reservoir 52 that may further aid fluid delivery (in addition to the irrigation source and/or the steady-state pressure of the filled compliant reservoir 52). The movement of the compliant reservoir adapter 53 and ensuing expansion of the compliant wall 18 is shown in FIG. 9C and FIG. 9D. When the oscillation is applied through the handset 1, the compliant reservoir adapter 53 oscillates which causes the compliant wall 18 to expand and contract. FIG. 9C illustrates the compliant reservoir adapter 53 in the fully retracted 56 position. Here the compliant reservoir 52 pressure is at a minimum and the compliant wall 18 is in its most relaxed state. The inner clearing catheter 21 is also fully retracted 56, since it oscillates in phase with the compliant reservoir adapter 53. FIG. 9D illustrates the compliant reservoir adapter 53 in the fully extended 57 position. When the compliant reservoir adapter 53 is in the fully extended 57 position the compliant reservoir 52 pressure is at a maximum and the compliant wall 18 is most expanded. The fluctuating pressure increase adds to the steady state pressure of the compliant reservoir 52 (comparable to the initial reservoir filling pressure or the fluid pressure supplied by an external irrigation source) pushes irrigation fluid towards the distal end of the outer sheath 22 in the space between the outer sheath 22 and inner clearing catheter 21. Due to the flow, irrigating droplets 62 exit the distal end of the outer sheath 22. The inner clearing catheter 21 is also in a fully extended 57 position at this point. The irrigating droplets 62 that are expelled from the end of the outer sheath 22 assist in clearing secretions 14.

Applies Universally to Clearing Catheter Designs 1 and 2

Mechanical oscillations 13 of the clearing catheter (10 or 20) aids in breaking up and clearing secretions in multiple ways, including but not limited to: agitation and mixing of the secretions with irrigation fluid to decrease viscosity for aspiration and shearing off or scraping of portions of secretions 14 when the tip of the clearing catheter (10 or 20) makes direct contact with the secretions 14 (including loosening material adherent with tube wall 9). Mechanical oscillation 13 of the clearing catheter (10 or 20) has other desirable effects, including but not limited to: reduced insertion force with less buckling of the clearing catheter 10 when inserted into the tube 9 (enabling narrower and more flexible clearing catheter design options and ability to insert while pushing with the handset 1, rather than having to feed the suction catheter 71 into the proximal end of tube 9 with fingers in close proximity to clearing catheter coupler 8 as is commonly practiced). Additionally, mechanical oscillations 13 may produce lateral modes of vibration that tend to re-establish or maintain aspiration flow within clearing catheter, especially when optimal length of clearing catheter (10 or 20) is pulled outside of tube 9. The lateral modes of vibration may also interact with the interior walls of tube 9 to help dislodge and agitate the secretions 14 that are located proximally to the distal tip of the clearing catheter (10 or 20). Once the secretions 14 are thinned or loosened by the irrigation flow 16 and mechanical oscillation 13, they are removed via aspiration flow 15 through an aspiration lumen (11 or 12) in the clearing catheter (10 or 20). The secretions 14 and other accumulating or occluding materials may be, but not limited to, mucus, blood, clots, or ingrown tissue/membranes. The clearing catheter (10 or 20) is of a multi-lumen design in order to accommodate both irrigation and aspiration, delivered locally at the working (distal) end of the clearing catheter (10 or 20).

When clearing secretions 14 from an ETT 9 using the present invention, the irrigation and aspiration applied at the distal tip of the clearing catheter 10 or 20 must be balanced in order to prevent irrigation fluid from entering or collecting in the lungs. The balancing of irrigation and aspiration at the distal tip of the clearing catheter 10 or 20 may be used with or without oscillation 13. Considerations for balancing irrigation and aspiration may include, but are not limited to, cross sectional area ratio of the lumens, fluid flow rate, and fluid velocity. Cross sectional area ratio is defined as the area of the aspiration lumen divided by the area of the irrigation lumen. Ideal cross sectional area ratios may range from 2:1 to 25:1, but more preferably from 10:1 to 20:1. Fluid flow rates are necessary to consider, since the fluid flow rate of the aspiration must be equal to the irrigation flow rate plus the desired flow rate of secretion removal. A factor of safety may also be incorporated into the flow rate design in order to increase confidence that all irrigation fluid is aspirated. As an additional effect to balance, aspiration flow rate cannot be too great, as it would reduce the pressure in the patient's lungs. Fluid velocity must be considered, since it largely predicts the strength of the irrigation and aspiration flows. Aspiration flow must be of higher velocity than the irrigation flow, so that the irrigation flow does not exit the effective area of aspiration. The strength of the aspiration flow must be greater than that of the irrigation flow. While each independent factor is important to consider, interactions between the factors must also be considered for different applications.

Figure 3A:
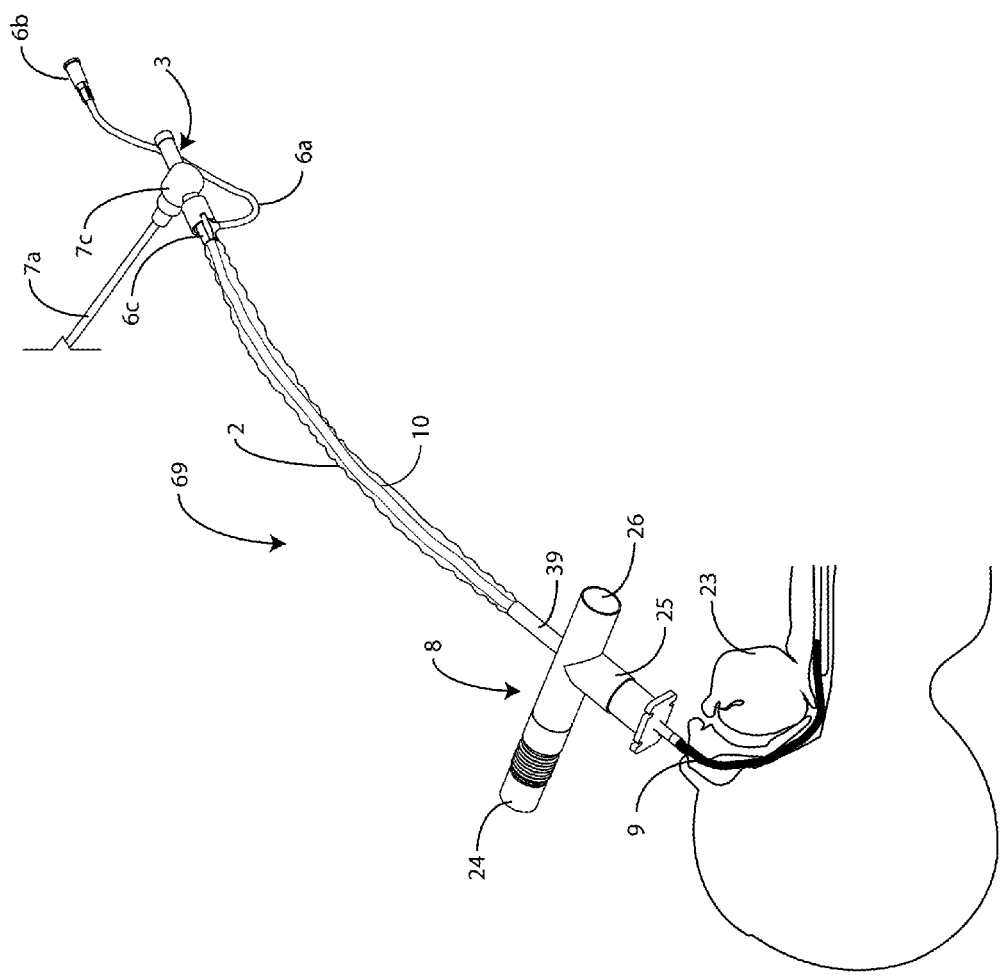
FIG. 3A shows how the clearing catheter is contained in a closed system within the airway tube (handset not attached).
Figure 3B:
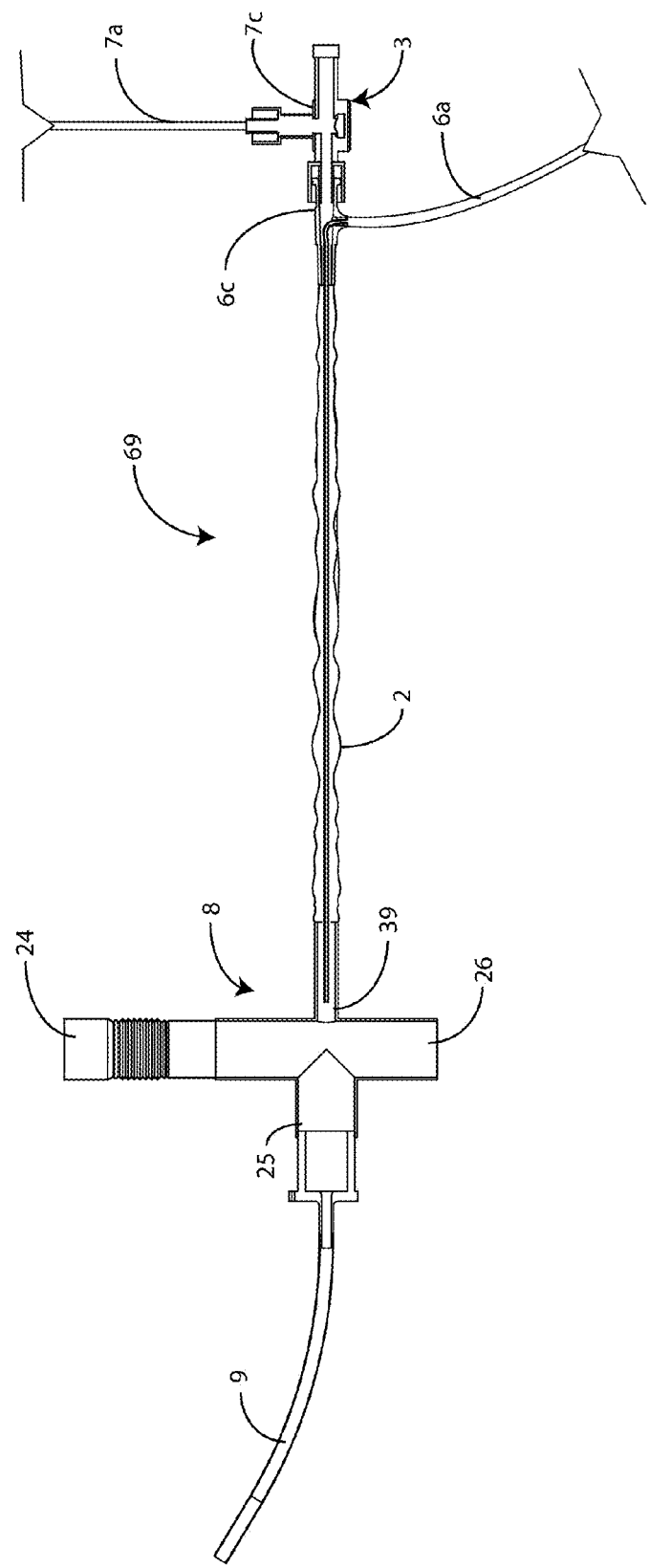
FIG. 3B shows a section view of the closed system and its inner components.
Figure 3C:
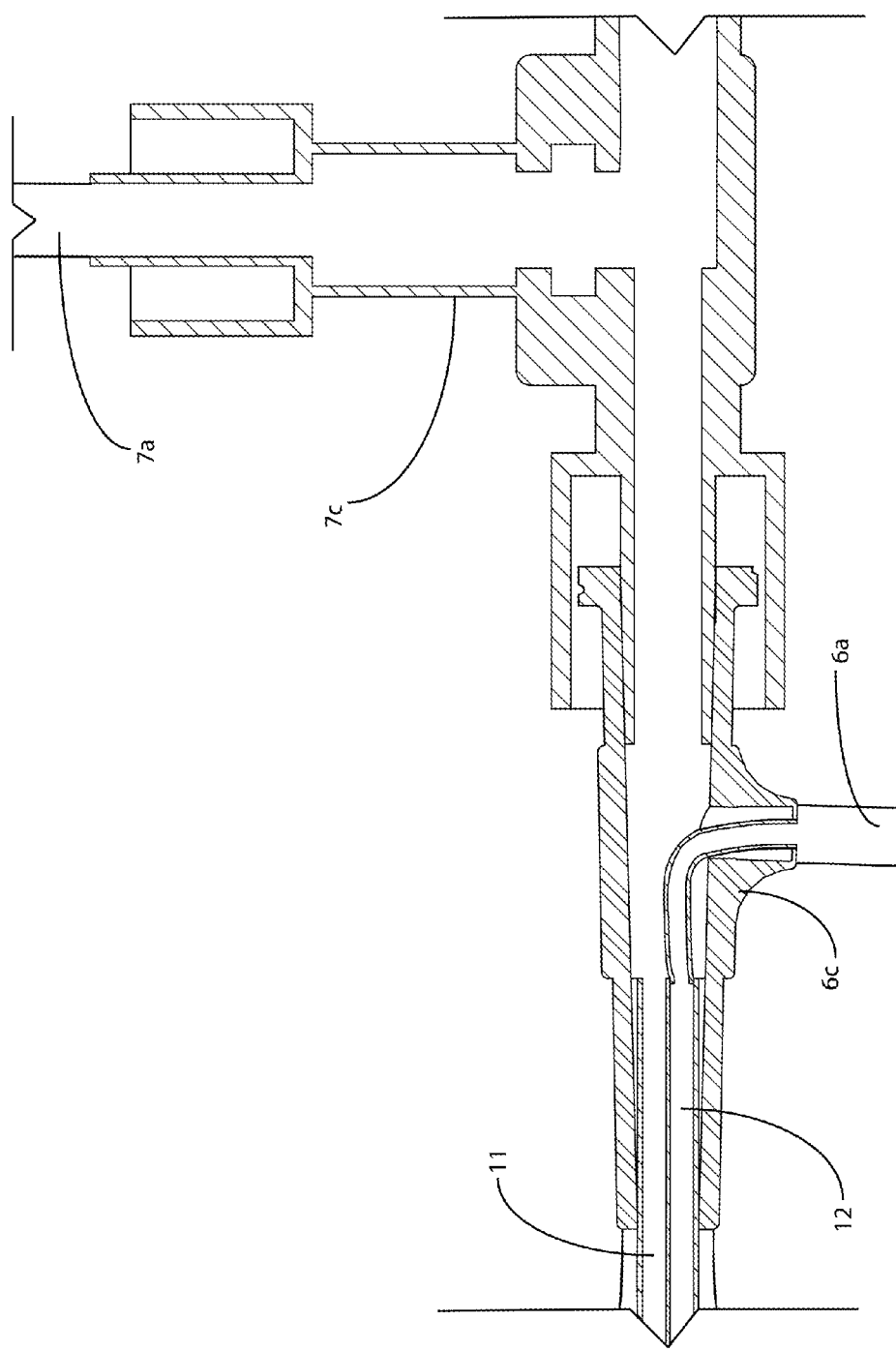
FIG. 3C shows a detailed section view of the catheter adapter at the proximal end of the clearing catheter demonstrating the separate irrigation and aspiration lumens and connection ports.

FIG. 3A through FIG. 3C illustrate how the closed clearing catheter system 69 (shown in FIGS. 3A and 3B) is implemented with regards to the patient 23 (shown in FIG. 3A), in both embodiments, CC1 and CC2, though specifically a closed clearing catheter system 69 and associated catheter adapter 3 (shown in FIGS. 3A and 3B) for CC1 is shown. The patient's 23 ETT 9 (shown in FIGS. 3A and 3B) is connected to the endotracheal tube port 25 (shown in FIGS. 3A and 3B) on a clearing catheter coupler 8 (shown in FIGS. 3A and 3B) which may have multiple ports, including but not limited to a ventilator port 24 (shown in FIGS. 3A and 3B), a clearing catheter port 39 (shown in FIGS. 3A and 3B), and an additional port 26 (shown in FIGS. 3A and 3B). The additional port 26 may be capped, used for a separate function, such as to wean the patient 23 off of assisted breathing, or not be present at all. The closed clearing catheter system 69 is attached to the clearing catheter port 39. Also, within clearing catheter port 39 there may be a seal (not shown), such as a slip fitting or possibly an adjustable valve such as a Tuohy-Borst adapter, for preventing the interior of the sterility sleeve 2 (shown in FIGS. 3A and 3B) from ventilating, particularly when a clearing catheter 10 or sheathed clearing catheter 20 is not inserted into the ETT 9 to clear secretions, but retracted and resting near patient's bedside while still connected to clearing catheter coupler 8, the purpose of this being to prevent air from shunting away from patient and into sterility sleeve 2 while being ventilated. A clearing catheter 10 or sheathed clearing catheter 20 is concentrically disposed on the inner bore of the clearing catheter port 39. A sterility sleeve 2 is concentrically disposed with regards to both the clearing catheter port 39 and clearing catheter 10 or 20, and seals exterior contaminants from entering the closed clearing catheter system 69. A catheter adapter 3 on the proximal end of the closed clearing catheter system 69 is connected to the sterility sleeve 2 and maintains the closed clearing catheter system 69 seal. Part of the catheter adapter 3 is an aspiration catheter coupler 7c and irrigation catheter coupler 6c which couples aspiration tubing 7a and irrigation tubing 6a, respectively. This tubing may extend to aspiration/irrigation sources or terminate in a connection, such as the irrigation connector 6b which can be secured to a source. For detail of lumen paths within the catheter adapter 3, see FIG. 3C.

Figure 4:
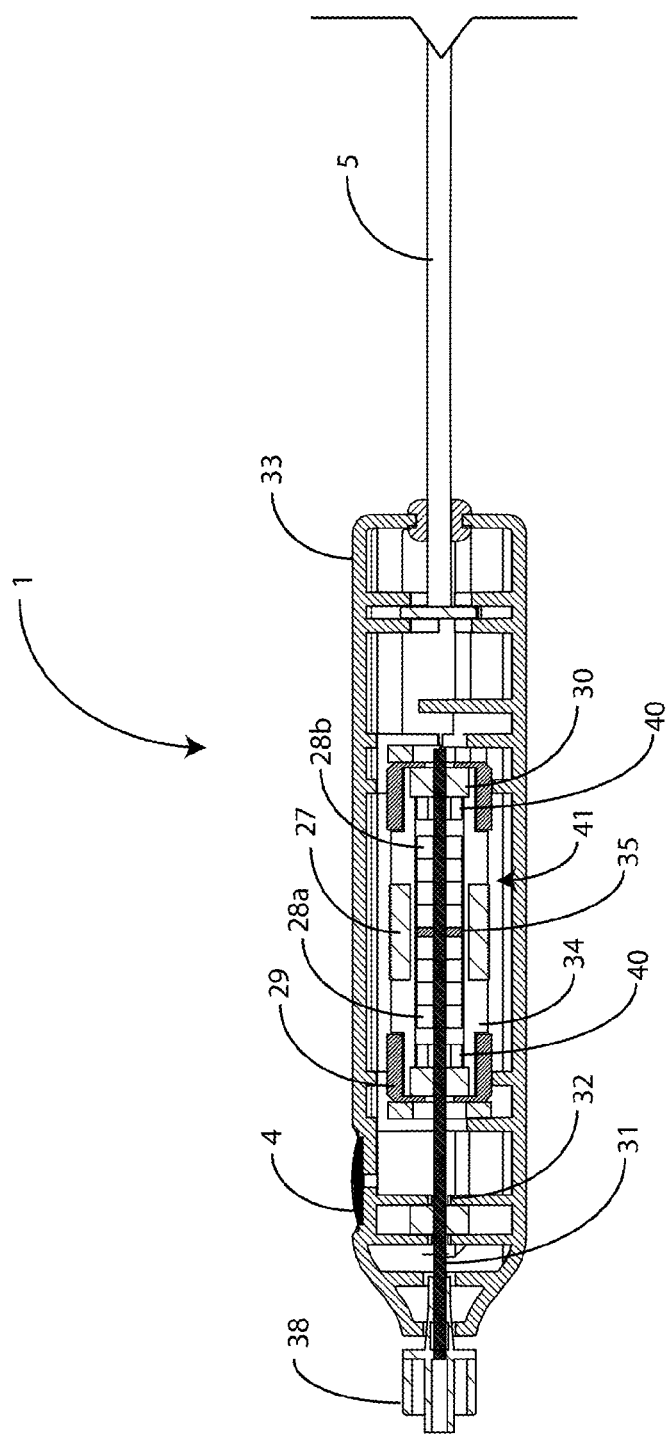
FIG. 4 illustrates a voice coil motor (VCM) handset, as one driving mechanism for delivering repetitive motion when attached to the clearing catheter via a keyed coupler.
Figure 5:
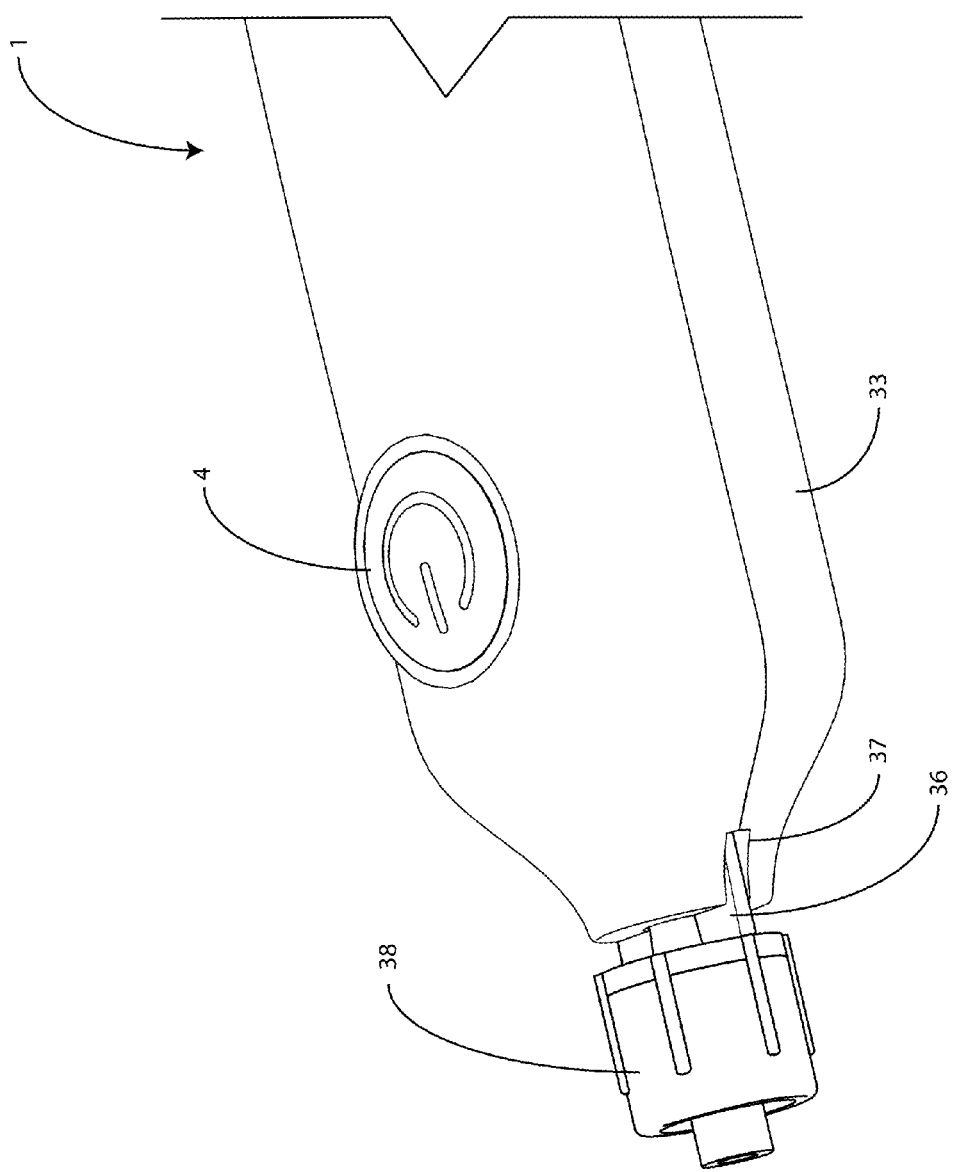
FIG. 5 shows the keyed coupler in detail.

Referring to FIG. 4, a handset 1 attaches to the clearing catheter 10 or 20 (not shown) via the catheter adapter 3 or magnet adapter 54, respectively (not shown). Inside the handset 1 is a voice coil motor (VCM) 41 which provides the oscillation energy which may be applied to the clearing catheter 10 or the sheathed clearing catheter 20. The VCM 41 provides the driving mechanism and consists of a cylindrical VCM body 34, with an embedded voice coil 27 disposed concentrically within. A magnet assembly 28a, adjacent to an opposing magnet assembly 28b with a pole piece 35 separating the two assemblies are fastened concentrically upon a displaceable shaft 31. Centering magnets 40 are attached to bearings 30, made from a low friction material such as but not limited to PTFE or Acetal, at the extreme ends of the VCM body 34. End caps 29 are present at each end to secure the entire assembly. The centering magnets 40 are magnets disposed in opposite polarization to the magnet assembly 28a and opposite magnet assembly 28b, and prevent collisions with the bearings 30 and end caps 29 while the shaft 31 is oscillating. The shaft 31 is routed through the distal end of the handset housing 33. Shaft guides 32 within the handset housing 33 maintain concentricity of the oscillating shaft 31. The shaft guides 32 may be integrated into the handset housing 33 design itself or may be inserts made of a specific low-friction material, such as but not limited to PTFE or Acetal. The distal end of the shaft 31 is connected to a keyed coupler 38, which attaches to the catheter adapter 3 on the clearing catheter 10 or the magnet adapter 54 of the sheathed clearing catheter 20 (not shown). A power cable 5 is routed through the proximal end of the handset housing 33, providing alternating current electrical energy to the voice coil 27. A power button 4 is pressed by the operator to control ON/OFF function of the handset 1. In order to keep the shaft 31 of the VCM 41 from rotating during operation, FIG. 5 illustrates a keyed coupler 38 with integrated keys 36, which slide within a keyway 37, which is integrated into the handset housing 33. The keys 36 and keyway 37 keep the shaft 31 from freely rotating when oscillating. Although shown as employing a VCM 41, it is to be understood that in accordance with other exemplary embodiments that the handset 1 may use various types of motors or components to create the vibratory motion.

Figure 8:
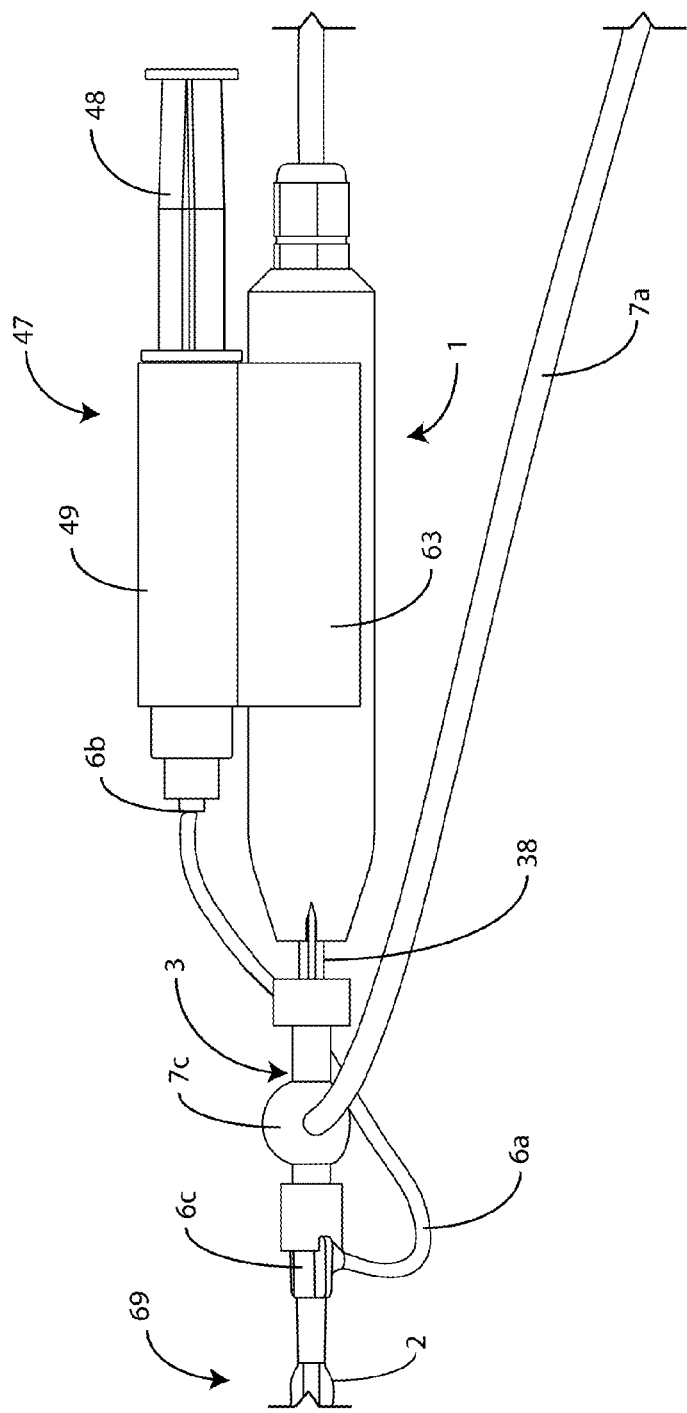
FIG. 8 shows the integration of a syringe to serve as irrigation source.
Figure 10:
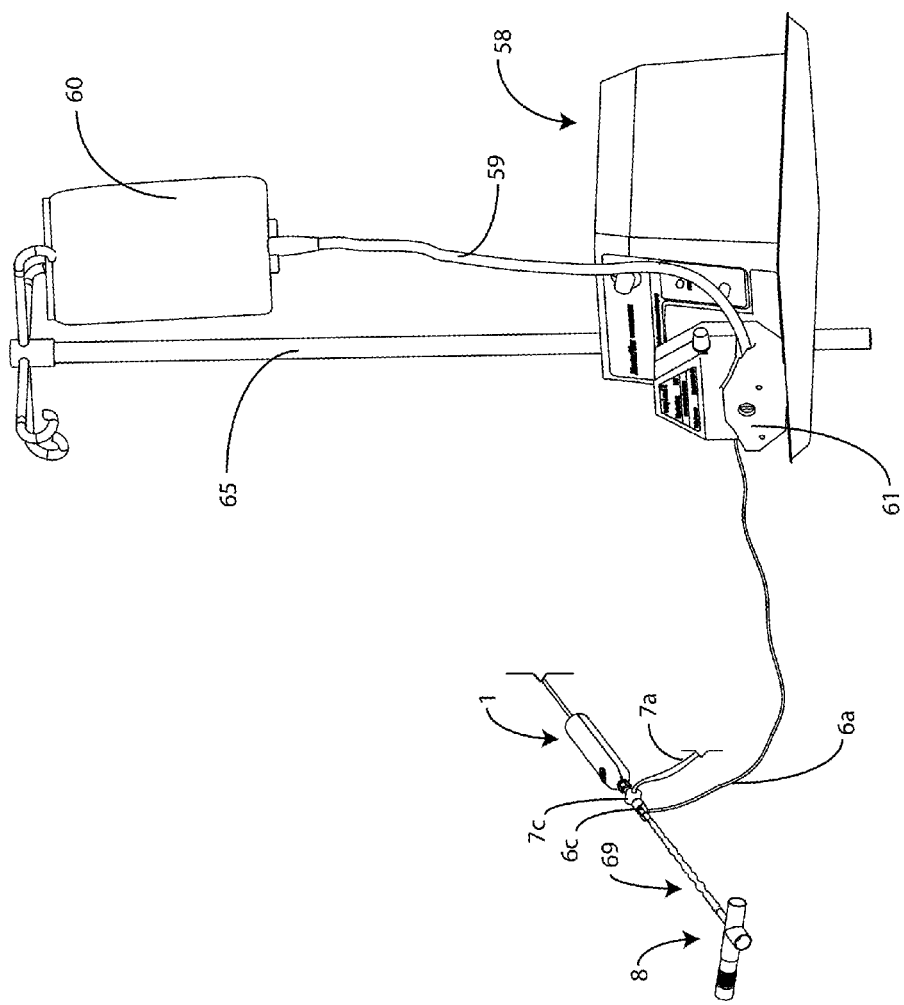
FIG. 10 illustrates the use of a peristaltic pump to provide irrigation flow.

FIG. 8 and FIG. 10 illustrate methods for the integration of accessory equipment which facilitate the function of, but not limited to, aspiration or irrigation to CC1 and CC2. The integration of a syringe 47 is shown in FIG. 8. The syringe 47 attaches to irrigation tubing 6a via an irrigation connector 6b to the closed clearing catheter system 69. The irrigation catheter coupler 6c couples the irrigation tubing 6a to the irrigation lumen 12 (not shown) in the clearing catheter 10 (not shown) or sheathed clearing catheter 20 (not shown). The syringe 47 is coupled to the handset 1 via a syringe coupling bracket 63 which attaches to the syringe body 49. Flow is controlled by applying pressure to the plunger 48 either by manual or automatic means. Automatic means may be, but not limited to, mechanical syringe pumps utilizing a pre-loaded spring or an electric motor/actuator which advances the plunger 48 within the syringe body 49, creating pressure and flow through the irrigation tubing 6a.

FIG. 10 illustrates the use of a peristaltic pump 58 to provide irrigation flow to the closed clearing catheter system 69. Fluid, such as saline, is held in a fluid reservoir 60. Pump tubing 59 attaches from the fluid reservoir 60 and passes through a pump housing 61. The pump housing 61 on a peristaltic pump 58 facilitates the easy replacement of pump tubing 59, eliminating contamination of the pump between uses, and the use of disposable fluid reservoirs 60 and pump tubing 59. After passing through the pump housing 61, the pump tubing 59 is routed into the closed clearing catheter system 69 as irrigation tubing 6a via an irrigation catheter coupler 6c.

Figure 11:
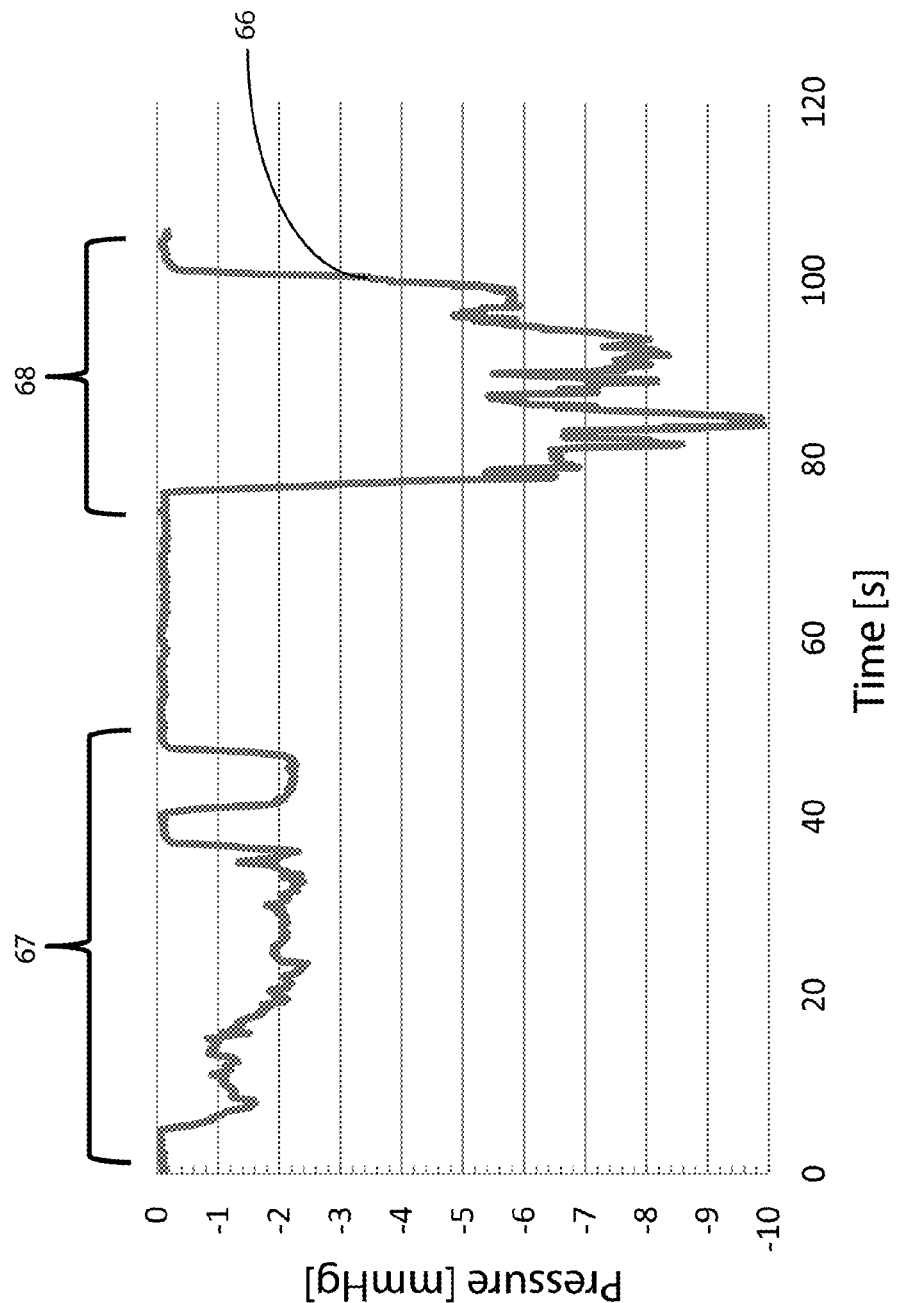
FIG. 11 shows a plot illustrating the advantages of the active clearing catheter system over a conventional suction catheter.

FIG. 11 illustrates the advantages to the patient from using the current embodiment 67 versus a standard 5 Fr suction catheter 68. A plot of pressure data 66 versus time is shown for both the current embodiment 67 and a standard 5 Fr suction catheter 68. The data was taken in a constant volume varying only the device used to clear the ETT. The pressure drop is significantly smaller in the current embodiment 67 than the standard 5 Fr suction catheter 68. Since the volumes of both experiments were held constant, the flow rate due to pressure drop is also proportional, showing that the present embodiment has less of an effect on the patient since less airflow is being taken from the lungs.

Additional lumens may be added whose functions may include, but are not limited to, a lumen for delivery of supplemental air and/or oxygen, sensing capability, or sampling functions. The lumen delivering supplemental air assists in replacing lost airway capacity due to the presence of the clearing catheter in the tube. Sensing functions may include, but are not limited to, oxygen content measurement or lung flow rate measurements. Sampling functions may include, but are not limited to, taking samples of air or secretions for composition or bacterial analysis. While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A device for removing materials from a tube, comprising:
    a clearing catheter having an outer sheath and an inner catheter forming an aspiration lumen and an irrigation lumen;
    a driving mechanism in mechanical communication with said inner catheter, applying reciprocating motion to said inner catheter such that said inner catheter reciprocates relative to said outer sheath;
    a compliant reservoir in fluid communication with said irrigation lumen and in mechanical communication with said driving mechanism, wherein said reciprocating motion of said driving mechanism causes changes in pressure in said compliant reservoir and said irrigation lumen; and
    a bracket restraining said outer sheath from said reciprocating motion.

2. The device as set forth in claim 1, wherein said inner catheter is located concentrically within said outer sheath, wherein said aspiration lumen is defined within the inner space of said inner catheter and said irrigation lumen is defined in a radial space between said outer sheath and said inner catheter.

3. The device as set forth in claim 1, wherein said- driving mechanism has a shaft with a distal end that reciprocates in a longitudinal direction; and a keyed coupler slidably affixed to said handset housing and connects to said distal end of said shaft, limiting rotational movement of said shaft during reciprocating motion of said shaft.

4. The device as set forth in claim 1, further comprising a handset housing including said driving mechanism, wherein said bracket is mounted to said handset housing.

5. The device as set forth in claim 1, wherein said aspiration lumen extends through said compliant reservoir, providing fluidic separation of an interior of said aspiration lumen from said compliant reservoir.

6. The device as set forth in claim 1, wherein said compliant reservoir is in fluid communication with an irrigation port through which irrigation fluid is introduced, and further comprising a compliant reservoir adaptor interposed between said driving mechanism and said compliant reservoir to transmit said reciprocating motion to said compliant reservoir, and in fluid communication with said aspiration lumen and including an aspiration port through which aspirated material exits.

7. The device as set forth in claim 1, wherein said clearing catheter has an interior space divided into coaxial irrigation and aspiration lumens.

8. The device as set forth in claim 1, further comprising a bracket adapter restrainingly interposed between said bracket and said outer sheath, and having an irrigation port in fluid communication with said compliant reservoir and said irrigation lumen.

9. The device as set forth in claim 8, wherein said aspiration lumen extends through and is fluidically separate from said compliant reservoir and said bracket adapter.

10. A device for removing materials from a tube, comprising:
- a clearing catheter having an aspiration lumen and an irrigation lumen;
- a dual lumen connector in fluid communication with said aspiration and irrigation lumens, said dual lumen connector having selectively attachable male and female components interconnecting said aspiration lumen and irrigation lumen respectively with aspiration and irrigation tubing;
- a first coupler connecting said aspiration lumen and a first portion of aspiration tubing;
- a second coupler connecting said irrigation lumen and a first portion of irrigation tubing;
- said male component of said dual lumen connector receiving said first portions of said irrigation tubing and said aspiration tubing;
- said female component of said dual lumen connector receiving second portions of said irrigation tubing and said aspiration tubing; and
- a driving mechanism that applies repetitive motion to said clearing catheter.

11. The device as set forth in claim 10, further comprising a clearing catheter coupler connecting said tube and said clearing catheter, wherein said tube, said clearing catheter coupler, said clearing catheter and said driving mechanism collectively define a closed system.

12. The device as set forth in claim 10, wherein said driving mechanism is at least one of a voice coil motor, a piezoelectric actuator, a pneumatic actuator, and a direct current motor.

13. The device as set forth in claim 10, further comprising:
- a handset housing including said driving mechanism, wherein said driving mechanism includes a shaft that reciprocates in a longitudinal direction and has a distal end; and
- a keyed coupler slidably affixed to said handset housing and connects to said distal end of said shaft, limiting rotational movement of said shaft during reciprocating motion of said shaft.

14. The device as set forth in claim 10, further comprising a brush located at a distal end of said clearing catheter.

15. The device as set forth in claim 10, wherein said clearing catheter has an interior space divided into parallel irrigation and aspiration lumens.

16. The device as set forth in claim 10, wherein said first and second couplers are located proximal to said driving mechanism.

17. A device for removing materials from a tube, comprising:
- a clearing catheter having an aspiration lumen and an irrigation lumen;
- a dual lumen connector in fluid communication with said aspiration and irrigation lumens, said dual lumen connector having selectively attachable male and female components interconnecting said aspiration lumen and irrigation lumen respectively with aspiration and irrigation tubing;
- wherein said female component receives said aspiration and said irrigation lumens, said male component receives irrigation tubing and aspiration tubing, and said male and female components are disposed in inline fluidic communication with said clearing catheter;
- a driving mechanism that applies repetitive motion to said clearing catheter; and,
- further comprising a handset housing including said driving mechanism, wherein said male component of said dual lumen connector attaches to said handset housing and said female component of said dual lumen connector attaches at said clearing catheter.

18. The device as set forth in claim 17, further comprising a clearing catheter coupler connecting said tube and said clearing catheter, wherein said tube, said clearing catheter coupler, said clearing catheter and said driving mechanism collectively define a closed system.

19. The device as set forth in claim 17, wherein said driving mechanism is at least one of a voice coil motor, a piezoelectric actuator, a pneumatic actuator, and a direct current motor.

20. The device as set forth in claim 17, further comprising:
- a handset housing including said driving mechanism, wherein said driving mechanism includes a shaft that reciprocates in a longitudinal direction and has a distal end; and
- a keyed coupler slidably affixed to said handset housing and connects to said distal end of said shaft, limiting rotational movement of said shaft during reciprocating motion of said shaft.

21. The device as set forth in claim 17, further comprising a brush located at a distal end of said clearing catheter.

22. The device as set forth in claim 17, wherein said clearing catheter has an interior space divided into parallel irrigation and aspiration lumens.

* * * * *